United States Patent [19]

Fukunaga et al.

[11] Patent Number: 5,091,297

[45] Date of Patent: Feb. 25, 1992

[54] SILVER HALIDE COLOR PHOTOGRAPHIC MATERIAL

[75] Inventors: Hiroo Fukunaga; Nobuo Furutachi; Genichi Furusawa, all of Kanagawa, Japan

[73] Assignee: Fuji Photo Film Co., Ltd., Kanagawa, Japan

[21] Appl. No.: 533,570

[22] Filed: Jun. 5, 1990

Related U.S. Application Data

[63] Continuation-in-part of Ser. No. 353,372, May 17, 1989, abandoned.

[30] Foreign Application Priority Data

May 17, 1988 [JP] Japan .................................. 63-118075

[51] Int. Cl.$^5$ .............................................. G03C 7/38
[52] U.S. Cl. ................................... 430/558; 430/384; 430/385
[58] Field of Search ............... 430/558, 386, 387, 552, 430/553, 384, 385

[56] References Cited

U.S. PATENT DOCUMENTS

| | | | |
|---|---|---|---|
| 3,725,067 | 4/1973 | Bailey et al. | 430/558 |
| 4,675,275 | 6/1987 | Nishijama et al. | 430/558 |
| 4,873,183 | 10/1989 | Tachibana et al. | 430/550 |
| 4,916,051 | 4/1990 | Tachibana et al. | 430/558 |

FOREIGN PATENT DOCUMENTS

| | | | |
|---|---|---|---|
| 0034950 | 9/1981 | European Pat. Off. | |
| 0252288 | 1/1988 | European Pat. Off. | |
| 0287265 | 10/1988 | European Pat. Off. | 430/558 |
| 1167840 | 7/1989 | Japan | 430/558 |
| 1172956 | 7/1989 | Japan | 430/558 |

OTHER PUBLICATIONS

Patent Abstracts of Japan, vol. 12, No. 163 (P-703)(3010), May 18, 1988, Abstracting JP-A-62 278552 (Konoshiroku) 03.12.1987 (Cat. A).
Mees & James, "The Theory of the Photographic Process", 3rd Ed., p. 387.

*Primary Examiner*—Charles L. Bowers, Jr.
*Assistant Examiner*—Lee C. Wright
*Attorney, Agent, or Firm*—Sughrue, Mion, Zinn, Macpeak & Seas

[57] ABSTRACT

A silver halide color photographic material comprising a support having thereon at least one silver halide red-sensitive emulsion layer containing at least one cyan coupler represented by formula (I) or (II)

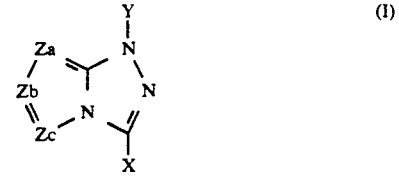

(I)

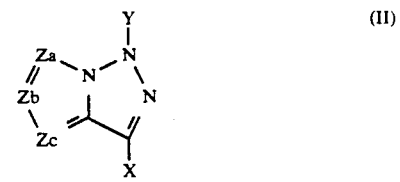

(II)

wherein Za represents

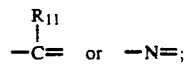

$-C=$ or $-N=$;

Zb represents

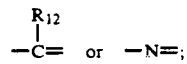

$-C=$ or $-N=$;

Zc represents

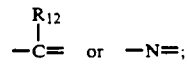

$-C=$ or $-N=$;

Y represents a hydrogen atom or a blocking group; X represents a hydrogen atom or a group which releases upon a reaction with an oxidation product or an aromatic primary amine color developing agent; $R_{11}$ represents a group which is substantially not released upon reaction with an oxidation product of an aromatic primary amine color developing agent; $R_{12}$ represents a hydrogen atom or a substitutent; or $R_{11}$, or $R_{12}$ or X may form a dimer, oligomer or polymer.

The silver halide color photographic material containing the novel cyan coupler is excellent in color reproducibility and image preservability.

13 Claims, No Drawings

SILVER HALIDE COLOR PHOTOGRAPHIC MATERIAL

This is a continuation-in-part of application Ser. No. 07/353,372, filed May 17, 1989 now abandoned.

FIELD OF THE INVENTION

The present invention relates to a silver halide color photographic material having improved color reproducibility and image preservability. More particularly, it relates to a silver halide color photographic material having improved color reproducibility and image preservability and comprising a novel cyan coupler.

BACKGROUND OF THE INVENTION

It is well known that, an aromatic primary amine color developing agent oxidized with an exposed silver halide reacts with a coupler to form a dye such as an indophenol, an indoaniline, an indamine, an azomethine, a phenoxazine, a phenazine or a like dye, to thereby form a color image. In this type of photographic system, the subtractive color process is ordinarily employed for color reproduction and color images are formed using yellow, magenta and cyan dyes.

In order to form cyan color images, phenolic or naphtholic couplers are generally employed. However, color reproducibility is remarkably deteriorated since dyes formed from these couplers have undesirable absorption in the green light region.

In order to solve this problem, 2,4-diphenylimidazoles have been proposed as described in European Patent 249,453. These couplers are preferred for color reproduction since they provide dyes having less undesirable absorption on the shorter wavelength side in comparison with conventional dyes.

However, the couplers as described in European Patent 249,453 are disadvantages in practical use because they have a low coupling activity, the hue of the dyes formed therefrom is unsatisfactory and the dyes formed therefrom have very poor fastness to heat and light (image preservability).

SUMMARY OF THE INVENTION

Therefore, an object of the present invention is to provide a silver halide color photographic material excellent in color reproducibility and image preservability.

Another object of the present invention is to provide a novel cyan coupler which forms a dye having little subsidiary absorption and excellent fastness to heat and light.

Other objectives of the present invention are apparent from the following detailed description and examples.

The objectives of the present invention are accomplished by a silver halide color photographic material comprising a support having thereon at least one silver halide red-sensitive emulsion layer containing at least one cyan coupler represented by formula (I) or (II)

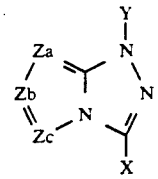

(I)

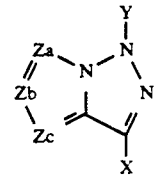

(II)

where Za represents

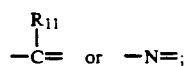

Zb represents

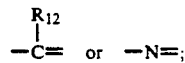

Zc represents

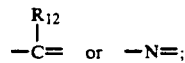

Y represents a hydrogen atom or a blocking group; X represents a hydrogen atom or a group which releases upon reaction with an oxidation product of an aromatic primary amine color developing agent; $R_{11}$ represents a group which is substantially not released upon reaction with an oxidation product of an aromatic primary amine color developing agent; $R_{12}$ represents a hydrogen atom or a substituent; or $R_{12}$, $R_{14}$ or X may form a dimer, oligomer or polymer.

DETAILED DESCRIPTION OF THE INVENTION

The cyan coupler represented by formula (I) or (II) is explained in more detailed below.

In formula (I) or (II), $R_{11}$ represents a group which is bonded at a carbon atom (for example, an alkyl group, an aryl group, a heterocyclic group, a cyano group, a carbamoyl group, an acyl group, an alkoxycarbonyl group, an aryloxycarbonyl group), a sulfamoyl group, a sulfonyl group or a sulfinyl group and $R_{12}$ represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group or an aryloxycarbonyl group.

More specifically, $R_{11}$ represents an alkyl group (for example, methyl, propyl, isopropyl, t-butyl, trifluoromethyl, tridecyl, 3-(2,4-di-tert-amylphenoxy)propyl, alkyl, 2-dodecyloxyethyl, 3-phenoxypropyl, 2-hexylsulfonylethyl, 3-(2-butoxy-5-tert-hexylphenylsulfonyl)propyl, cyclopentyl, benzyl), an aryl group (for example, phenyl, 4-tert-butylphenyl, 2,4-di-tert-amylphenyl, 4-tetradecanamidophenyl), a heterocyclic group (for example, 2-furyl, 2-thienyl, 2-pyrimidinyl, 2-benzothiazolyl), a cyano group, a carbamoyl group (for example, N-ethylcarbamoyl, N,N-dibutylcarbamoyl, N-(2-dodecyloxyethyl)carbamoyl, N-methyl-N-dodecycarbamoyl, N-(3-(2,4-di-tert-amylphenoxy)propyl)carbamoyl), an acyl group (for example, acetyl, (2,4-di-tert-amylphenoxy)acetyl, benzoyl), an alkoxycarbonyl group (for example, methoxycarbonyl, butyloxycarbonyl, dodecyloxycarbonyl, octadecyloxycarbonyl), an aryloxycarbonyl group (for example, phenyloxycarbonyl, 3-pentadecylphenoxycarbonyl), a sulfamoyl group (for example, N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a sulfonyl group (for example, methanesulfonyl, octanesulfonyl, benzenesulfonyl, toluenesulfonyl, 2-butoxy-5-tert-octylphenylsulfonyl), and a sulfinyl group (for example, octanesulfinyl, dodecylsulfinyl, phenylsulfinyl) and $R_{12}$ represents a hydrogen atom, a halogen atom (for example, chlorine, or bromine), an alkyl group (for example, methyl, propyl, isopropyl, tert-butyl, trifluoromethyl, tridecyl, 3-(2,4-di-tert-amyl phenoxy)propyl, allyl, 2-dodecyloxyethyl, 3-phenoxypropyl, 2-hexylsulfonylethyl, 3-(2-butoxy-5-tert-hexyl-phenylsulfonyl)propyl, cyclopentyl, benzyl), an aryl group (for example, phenyl, 4-tert-butylphenyl, 2,4-di-tert-amylphenyl, 4-tetradecanamidophenyl), a heterocyclic group (for example, 2-furyl, 2-thienyl, 2-pyrimidinyl, 2-benzothiazolyl), a cyano group, an alkoxy group (for example, methoxy, ethoxy, 2-methoxyethoxy, 2-dodecyloxyethoxy, 2-phenoxyethoxy, 2-methanesulfonylethoxy), an aryloxy group (for example, phenoxy, 2-methylphenoxy, 2-methoxyphenoxy, 4-tert-butylphenoxy), a heterocyclic oxy group (for example, 2-benzimidazolyloxy), an acyloxy group (for example, acetoxy, hexadecanoyloxy), a carbamoyloxy group (for example, N-phenylcarbamoyloxy, N-ethylcarbamoyloxy), a syliloxy group (for example, trimethylsilyloxy), a sulfonyloxy group (for example, dodecylsulfonyloxy), an acylamino group (for example, acetamido, benzamido, tetradecanamido, o-(2,4-di-tert-amylphenoxy)butyramido, γ-(3-tert-butyl-4-hydroxyphenoxy)butyramido, α-[4-(4- hydroxyphenylsulfonyl)phenoxy]decanamido), an anilino group (for example, phenylamino, 2-chloroanilino, 2-chloro-5-tetradecanamidoanilino, 2-chloro-5-dodecyloxycarbonylanilino, N-acetylanilino, 2-chloro-5-[α-(3-tert-butyl-4-hydroxyphenoxy)dodecanamido]anilino), a ureido group (for example, phenylureido, methylureido, N,N-dibutylureido), an imido group (for example, N-succinimido, 3-benzylhydrantoinyl, 4-(2-ethylhexanoylamino)phthalimido), a sulfamoylamino group (for example, N,N-dipropylsulfamoylamino, N-methyl-N-decylsulfamoylamino), an alkylthio group (for example, methylthio, octylthio, tetradecylthio, 2-phenoxyethylthio, 3-phenoxypropylthio, 3-(4-tert-butylphenoxy)propylthio), an arylthio group (for example, phenylthio, 2-butoxy-5-tert-octylphenylthio, 3-pentadecylphenylthio, 2-carboxyphenylthio, 4-tetradecanamidophenylthio), a heterocyclic thio group (for example, 2-benzothiazolylthio), an alkoxycarbonylamino group (for example, methoxycarbonylamino, or tetradecyloxycarbonylamino), an aryloxycarbonylamino group (for example, phenoxycarbonylamino, 2,4-di-tert-butylphenoxy carbonylamino), a sulfonamido group (for example, methanesulfonamido, hexadecanesulfonamido, benzenesulfonamido, p-toluenesulfonamido, octadecanesulfonamido, 2-methoxy-5-tert-butylbenzenesulfonamido), a carbamoyl group (for example, N-ethylcarbamoyl, N,N-dibutylcarbamoyl, N-(2-dodecyloxyethyl)carbamoyl, N-methyl-N-dodecylcarbamoyl, N-[3-( 2,4-d i-tert-amylphenoxy)propyl]carbamoyl), an acyl group (for example, acetyl, (2,4-di-tert-amylphenoxy)acetyl, benzoyl), a sulfamoyl group (for example, N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a sulfonyl group (for example, methanesulfonyl, octanesulfonyl, benzenesulfonyl, toluenesulfonyl, 2-butoxy-5-tert-octylphenylsulfonyl), a sulfinyl group (for example, octanesulfinyl, dodecylsulfinyl, phenylsulfinyl), an alkoxycarbonyl group (for example, methoxycarbonyl, butoxycarbonyl, dodecyloxycarbonyl, octadecyloxycarbonyl), or an aryloxycarbonyl group (for example, phenoxycarbonyl, 3-pentadecylphenoxycarbonyl).

In the general formula (I) or (II), X represents a hydrogen atom or a group which releases upon reaction with an oxidation product of an aromatic primary amine color developing agent. More specifically, the releasable group includes a halogen atom (for example, fluorine, chlorine, or bromine), an alkoxy group (for example, dodecyloxy, dodecyloxycarbonylmethoxy, methoxyethylcarbamoylmethoxy, carboxypropyloxy), an aryloxy group (for example, 4-methylphenoxy, 4-tert-butylphenoxy, 4-methoxyphenoxy, 4-methanesulfonylphenoxy, 4 - (4-benzyloxyphenylsulfonyl)phenoxy), an acyloxy group (for example, acetoxy, tetradecanoyloxy, benzoyloxy), a sulfonyloxy group (for example, methanesulfonyloxy, toluenesulfonyloxy), an amido group (for example, dichloroacetylamino, methanesulfonylamino, triphenylphosphonamido), an alkoxycarbonyloxy group (for example, ethoxycarbonyloxy, benzyloxycarbonyloxy.), an aryloxycarbonyloxy group (for example, phenoxycarbonyloxy), an aliphatic, aromatic or heterocyclic thio group (for example, phenylthio, dodecylthio, benzylthio, 2-butoxy-5-tert-octylphenylthio, 2,5-di-octyloxyphenylthio, 2-(2-ethoxyethoxy)-5-tert-octylphenylthio, tetrazolylthio), an imido group (for example, succinimido, hydantoinyl, 2,4-dioxooxazolidin-3-yl, 3-benzyl-4-ethoxyhydantoin-1-yl), an N-heterocyclic group (for example, 1-pyrazolyl, 1-benzotriazolyl, 5-chloro-1,2,4-triazol-1-yl), and an aromatic azo group (for example, phenylazo). The releasable group X may also contain a photographically useful group.

In formula (I) or (II), Y represents a hydrogen atom an acyl group having from 1 to 32 carbon atoms (for example, formyl, acetyl, benzoyl, chloroacetyl, trifluoroacetyl, furoyl), an alkyl or aryl sulfonyl group having from 1 to 32 carbon atoms (for example, mesyl, tosyl, dodecylsulfonyl), an alkyl or aryl oxycarbonyl group having from 1 to 32 carbon atoms (for example, methoxycarbonyl, phenoxycarbonyl), an acyloxymethylene group having from 2 to 32 carbon atoms (for example, acetoxymethylene, benzoyloxymethylene), a carbamoyl group having from 1 to 32 carbon atoms (for example, dimethylcarbamoyl, methoxyethylcarbamoyl, phenylcarbamoyl), or a group represented by formula (III):

wherein $Y_1$ and $Y_2$, which may be the same or different, each represents a nitro group, a cyano group, a carboxy group, an aryl group having from 6 to 32 carbon atoms (for example, 4-nitrophenyl, 4-cyanophenyl, 4-tetradecyloxyphenyl), a heterocyclic group having from 1 to 32 carbon atoms (for example, 1-tetrazolyl, 2-thiazolyl, benzothiazol-2-yl, benzoxazol-2-yl), an acyl group having from 1 to 32 carbon atoms (for example, acetyl, benzoyl, pivaloyl, trifluoroacetyl, 4-nitrobenzoyl), an alkyl or aryl oxycarbonyl group having from 1 to 32 carbon atoms (for example, methoxycarbonyl, ethoxycarbonyl, phenoxycarbonyl, dodecyloxycarbonyl), an alkyl or aryl sulfonyl group having from 1 to 32 carbon atoms (for example, mesyl, tosyl), a carbamoyl group having from 1 to 32 carbon atoms (for example, dimethylcarbamoyl, methylcarbamoyl, phenylcarbamoyl, 3,5-dicarboxyphenylcarbamoyl, 4-sulfophenylcarbamoyl), or a sulfamoyl group having from 0 to 32 carbon atoms (for example, methylsulfamoyl, phenylsulfamoyl).

In the explanation of formula (I), (II), or (III), the heterocyclic group is 5- to 7- membered, and the hetero atom is, e.g., nitrogen, oxygen, and sulfur.

Specific examples of the blocking group represented by formula (III) are described, for example, in U.S. Pat. No. 4,338,393, JP-A-58-108534, JP-A-58-111034, JP-A-58-111035, JP-A-58-111943, JP-A-58-111944, JP-A-58-113936 and JP-A-58-115437 (the term "JP-A" as used herein means an "unexamined published Japanese patent application").

In formula (I) or (II), $R_{11}$, $R_{12}$ and X, either individually or in combination, may form a coupler comprising a dimer, oligomer or polymer. When a dimer is formed, the group $R_{11}$ and/or $R_{12}$ and/or X may represent a single bond or a divalent linking group (for example, an alkylene group, an arylene group, an ether group, an ester group, an amido group or a combination thereof). When an oligomer or a polymer is formed, the group may represent the main chain of a polymer or a linking group connected with a main chain of a polymer through a divalent group as described for the dimer above. Further, the polymer coupler may be a homopolymer of the coupler derivative or a copolymer of the coupler derivative and at least one non-color forming ethylenic monomer (for example, acrylic acid, methacrylic acid, methyl acrylate, n-butylacrylamide, β-hydroxyethyl methacrylate, vinyl acetate, acrylonitrile, styrene, crotonic acid, maleic anhydride, or N-vinylpyrrolidone).

Y in the general formula (I) or (II), preferably represents a hydrogen atom, an acyl group having from 1 to 32 carbon atoms or a group represented by the general formula (III). Among them, a hydrogen atom is particularly preferred.

Of the compounds represented by the general formula (I) or (II), those represented by formula (IV), (V), (VI), (VII), (VIII), (IX), (X), (XI), (XII), (XIII), (XIV), (XV), (XVI) or (XVII) as described below are particularly preferred.

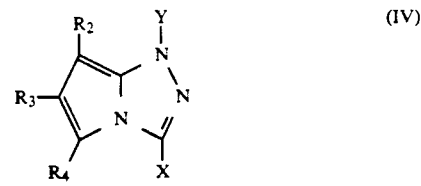

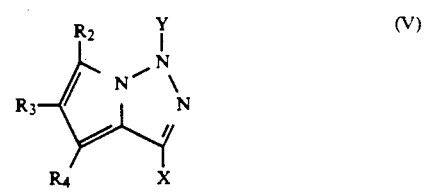

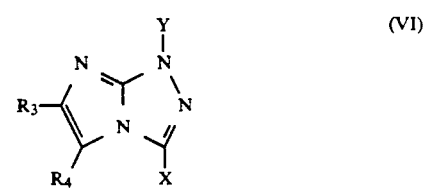

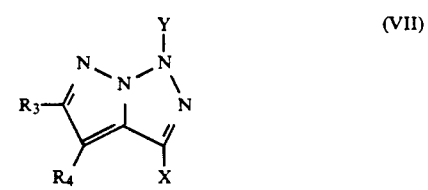

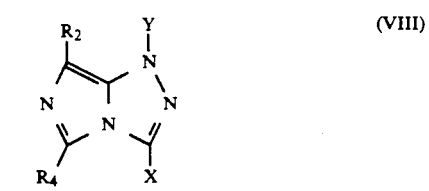

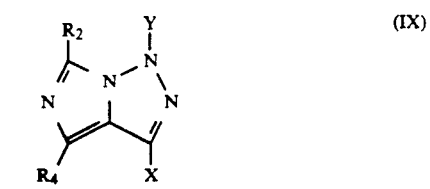

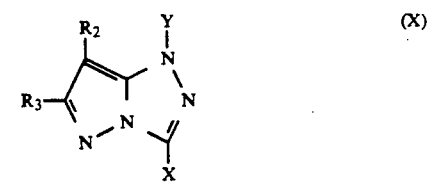

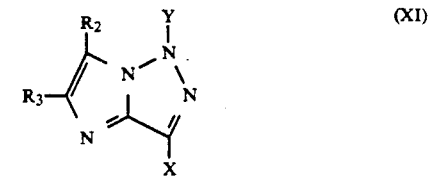

-continued

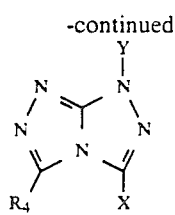 (XII)

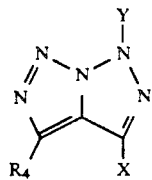 (XIII)

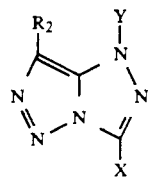 (XIV)

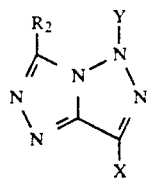 (XV)

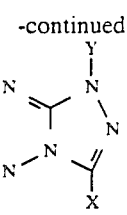 (XVI)

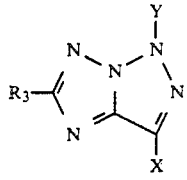 (XVII)

wherein in formulae (IV) to (XVII), $R_2$ has the same meaning as defined for $R_{11}$ in formula (I) or (II); $R_3$ has the same meaning as defined for $R_{12}$ in formula (I) or (II); and $R_4$ has the same meaning as defined for $R_{11}$ in formula (I) or (II). However, in formula (X), in a case where $R_2$ represents an alkoxycarbonyl group or an aryloxycarbonyl group, X does not represent an alkylthio group, a heterocyclic group, an acylamino group or an alkoxy group, and in a case where a dimer is formed by $R_2$, a bis type coupler is not formed by an alkylidene group.

The total number of carbon atoms included in $R_2$, $R_3$, $R_4$ and X in each of formulae (IV) to (XVII) is an amount that can make the compound nondiffusible and it is preferably 10 or more.

Specific examples of the compounds represented by formula (I) or (II) according to the present invention are set forth below, but the present invention should not be construed as being limited thereto.

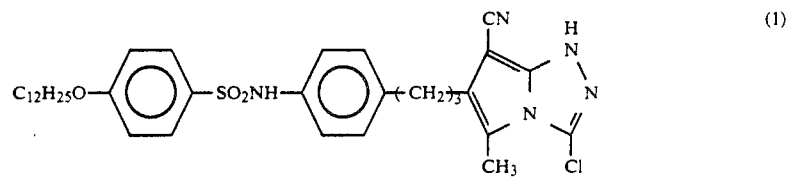 (1)

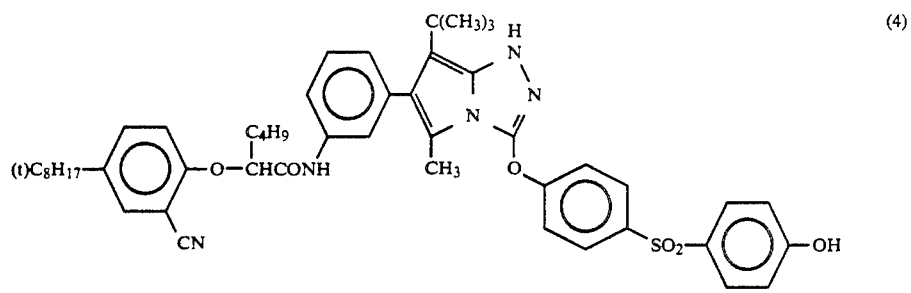 (4)

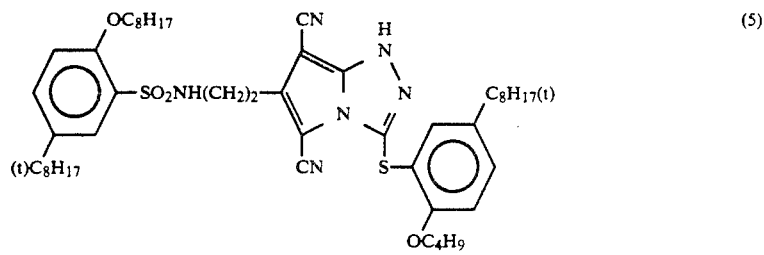 (5)

-continued
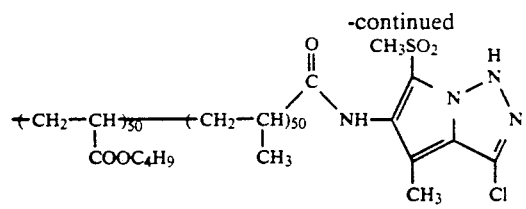
(6)
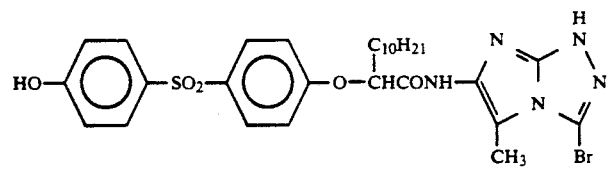
(8)
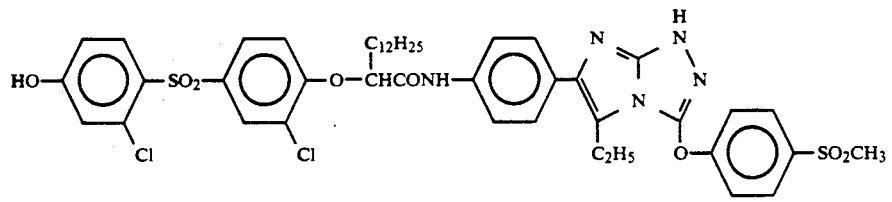
(9)
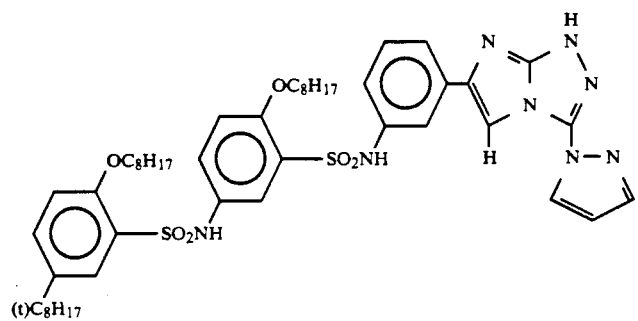
(10)
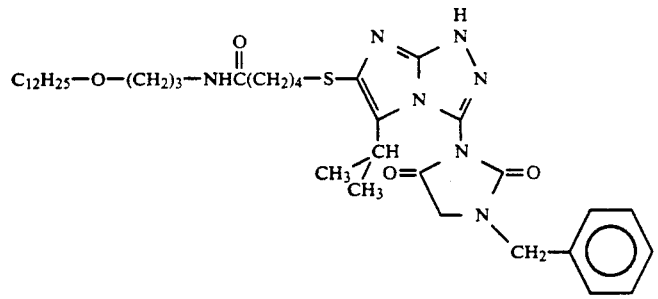
(11)
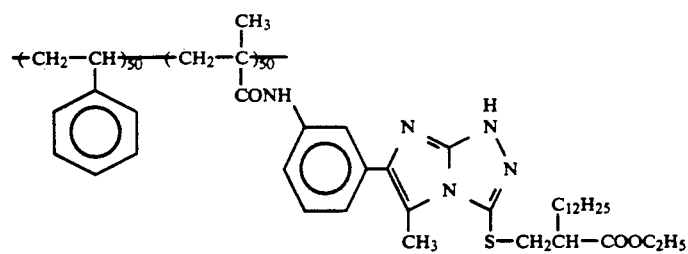
(12)
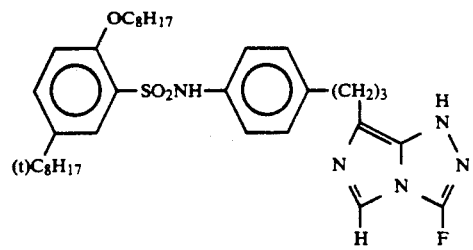
(13)

-continued
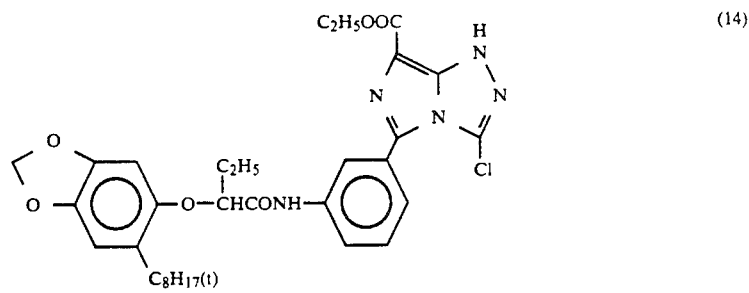
(14)
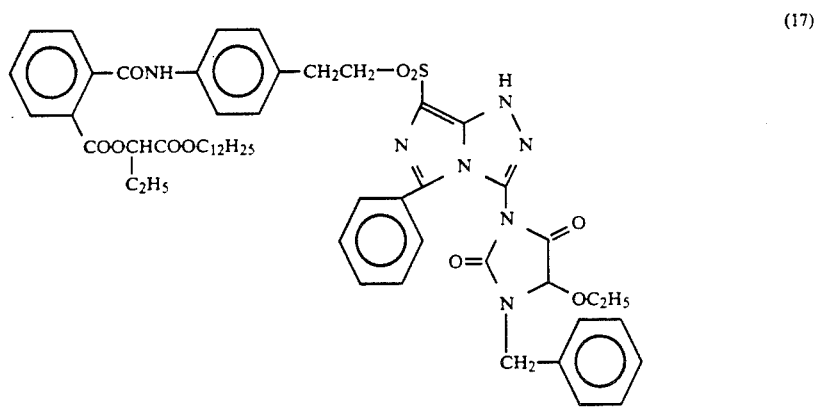
(17)
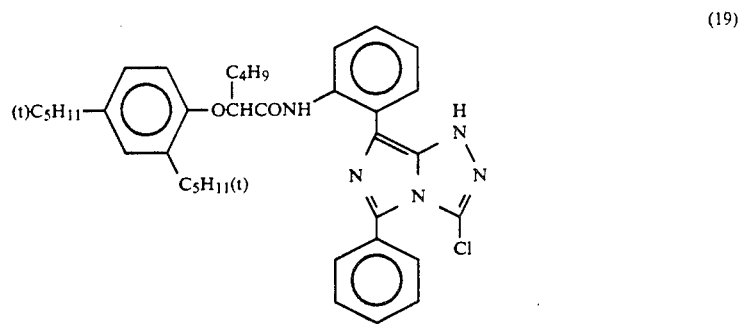
(19)
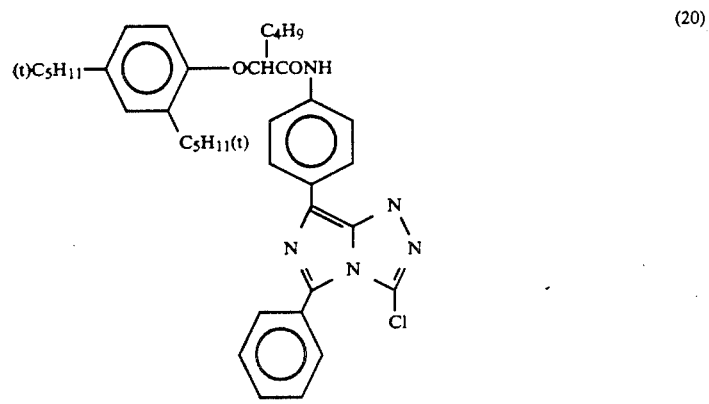
(20)

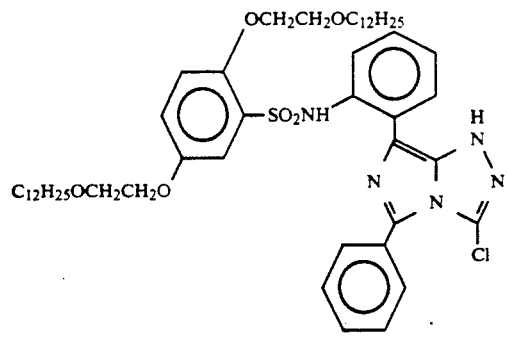
(21)
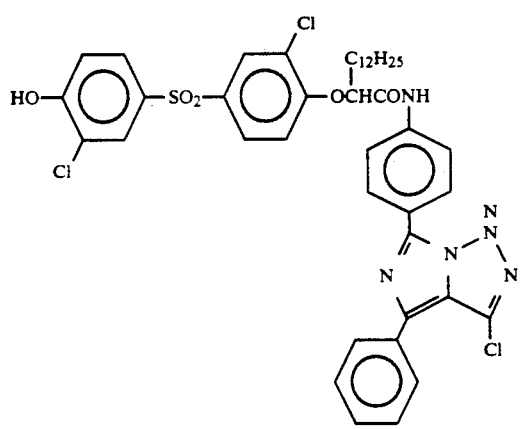
(22)
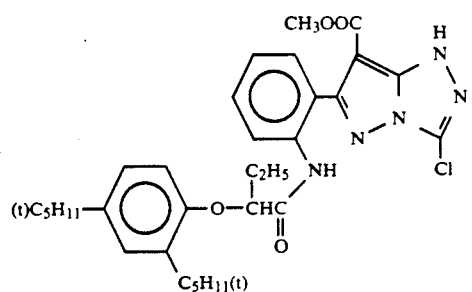
(23)
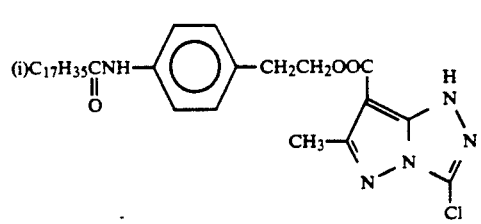
(24)
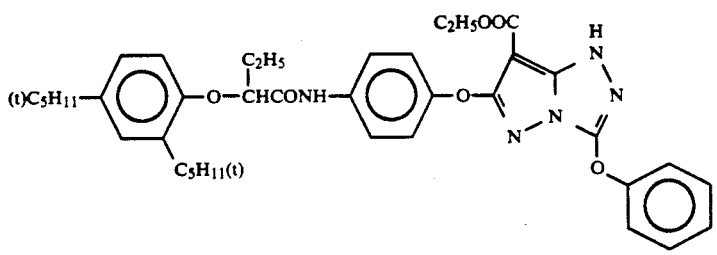
(25)

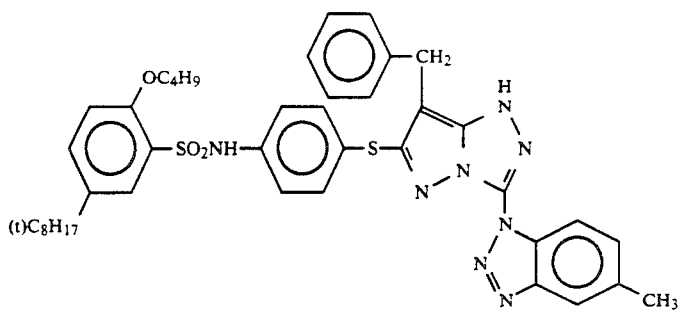
(26)
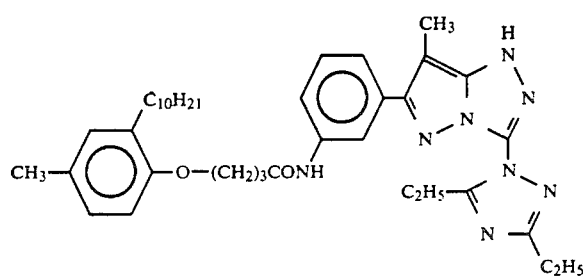
(27)
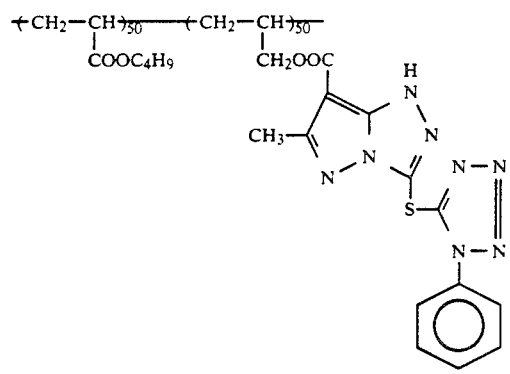
(28)
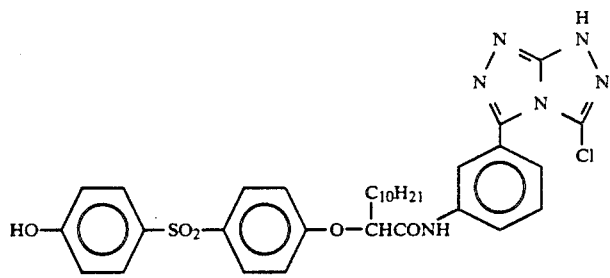
(30)
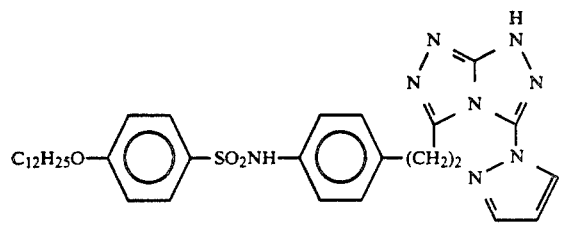
(32)

-continued
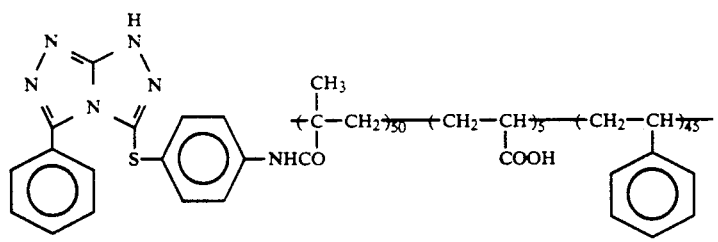 (34)
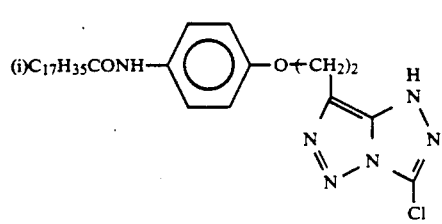 (35)
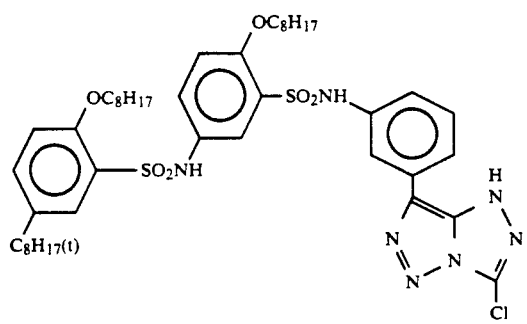 (36)
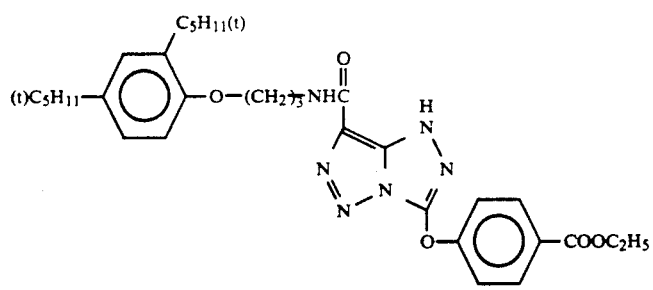 (37)
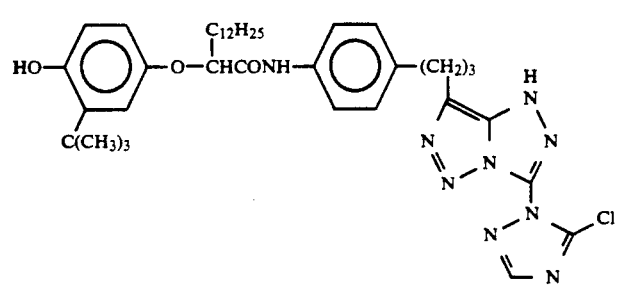 (38)

-continued
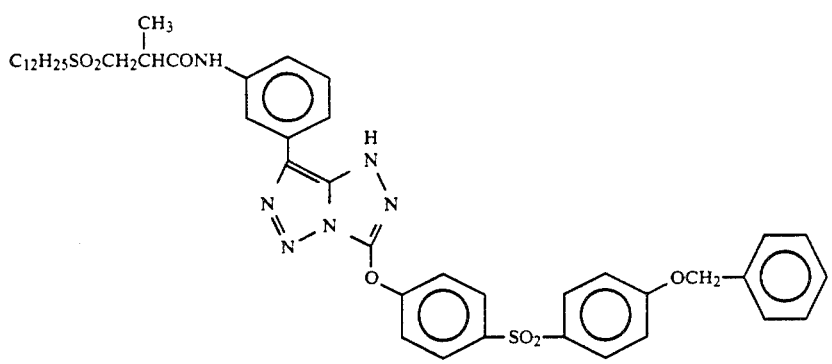 (39)
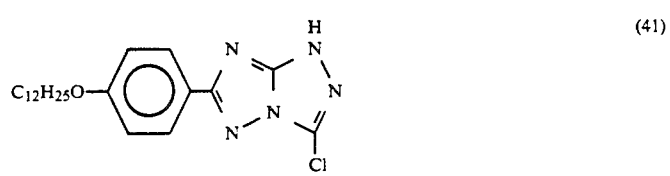 (41)
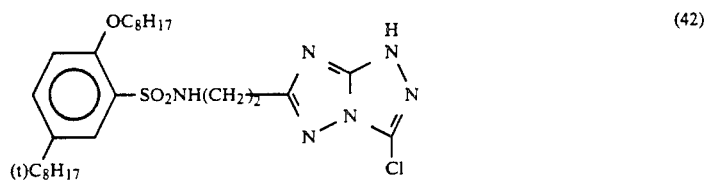 (42)
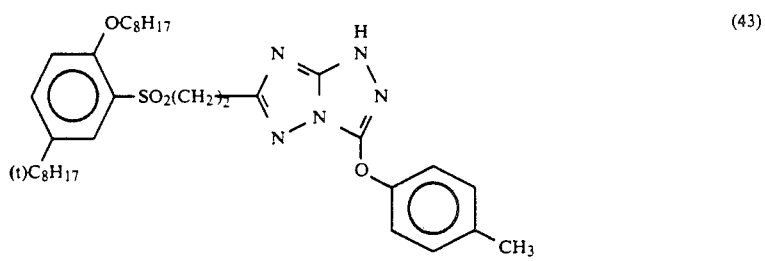 (43)
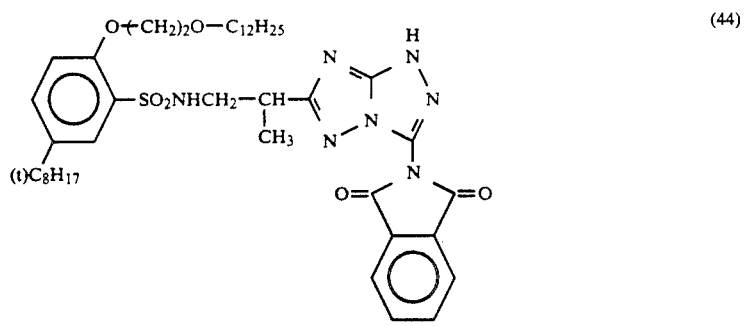 (44)
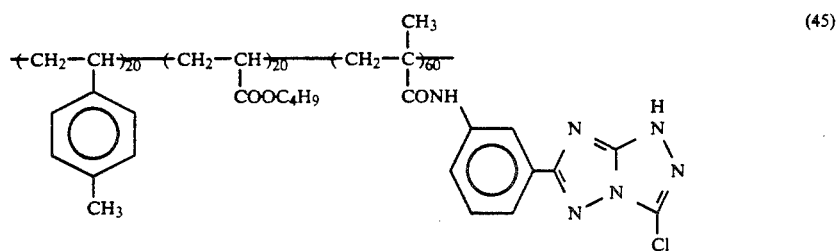 (45)

-continued

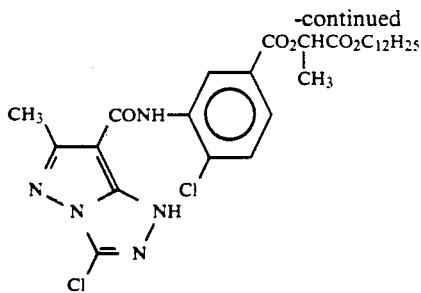 (46)

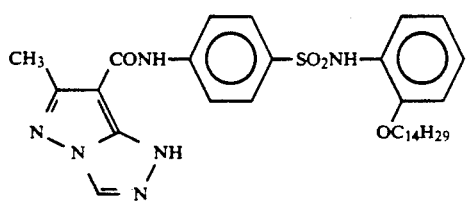 (47)

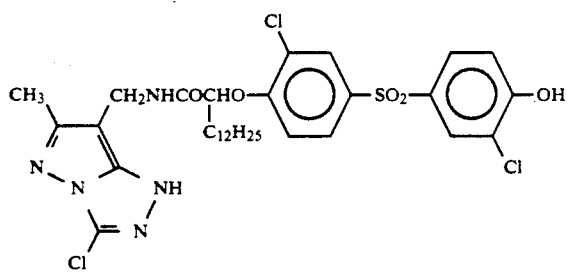 (48)

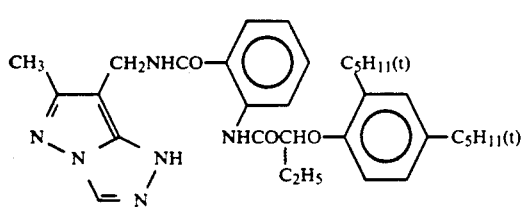 (49)

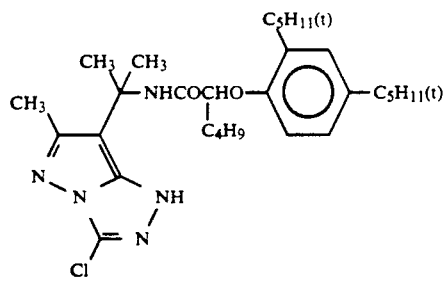 (50)

The couplers of the present invention can be synthesized according to the methods as described, for example, in U.S. Pat. No. 3,725,067, *J. Pract. Chem.*, Vol. 30, page 280 (1963), *J. Chem. Soc.*, Vol. 1957, page 727 (1957), or *J. Org. Chem.*, Vol. 33, page 143 (1968), or in a similar manner thereto.

More specifically, the compounds represented by formulae (I) and (II) are synthesized by the ring closure reaction according to the following scheme.

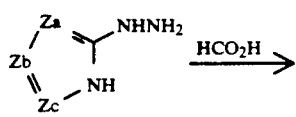

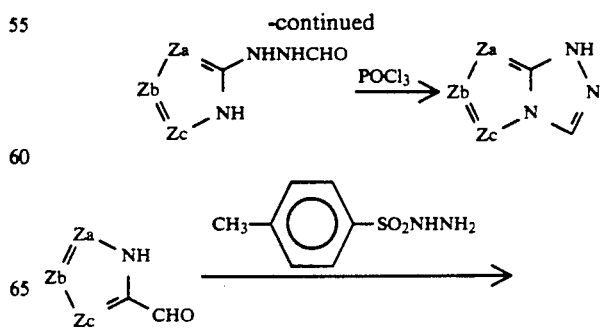

-continued

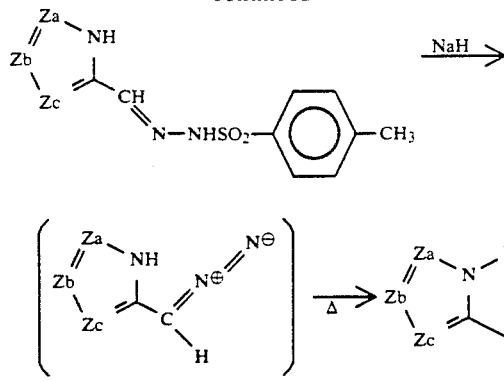

SYNTHESIS EXAMPLE

Synthesis of Coupler (47)

In accordance with the method of J. Bailey et al, 6-methyl-1H-pyrazolo[5,1-C][1,2,4]triazole-7-carboxylic acid ((4)) was synthesized as disclosed in J. Chem. Soc. Perkin Trans. I, 2047 (1977).

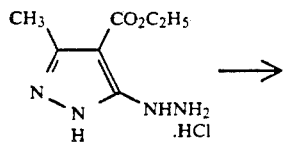

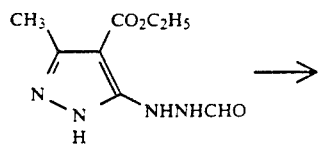

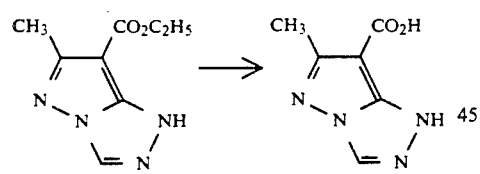

Specifically, 66.0 g (0.3 mol) of hydrazine hydrochloric acid salt ((1)) was dispersed in 300 ml of methanol, and 42.0 ml (0.3 mol) of triethylamine was added dropwise thereto under heating and reflux. After the dropwise additioin, the mixture was heated under reflux for 10 minutes. Thereafter, the mixture was returned to room temperature. The precipitated crystal was filtrated to obtain 43.2 g (0.235 mol) of free hydrazine. To the hydrazine 300 ml of acetonitrile and 15 ml of formic acid were added under heating and reflux for 4 hours. The mixture as returned to room temprerature to filtrate the precipitated crystal. Then, 44.4 g (0.21 mol) of formylhydrazine ((2)) was obtained. Further, 700 ml of dioxane and 42.0 ml of phosphorus oxychloride were added thereto, and the mixture was heated under reflux for 2 hours. The reaction mixture was returned to room temperature, pound into 2 liters of ice water, and the precipitated crystal was filtered to obtain 27.2 g (0.14 mol) of the compound ((3)). Next, 270 ml of concentrated sulfuric acid was added thereto and the mixture was stirred for 1 hour at an internal temperature of from 90° to 95 ° C. After return to room temperature, the reaction mixture was poured to ice water and the precipitated crystal was filtered to obtain 12.2 g of carboxylic acid ((4)).

3.3 g (0.02 mol) of the carboxylic acid ((4)) and 9.2 g (0.02 mol) of 4-(2-tetradecyloxyphenylsulfamoyl) aniline were dissolved into 60 ml of dimethylacetamide, and 6.0 g of dicyclohexylcarbodiimide was added thereto. Then the mixture was stirred for 3 hours at an internal temperature of from 86° to 90 ° C. The reaction mixture was returned to room temperature and 300 ml of ethyl acetate was added thereto. After filtration of the precipitated dicyclohexyl urea, ethyl acetate solution was washed three times and dried by Glauber's salt. The oily product obtained by distillation of solvent was crystallized by hexane and ethyl acetate mixed solvent to obtain 8.4 g of the intended coupler (47). Melting point: 183°–186 ° C.

Other couplers can be synthesized according to the above described synthesis method.

According to the following scheme, the coupler represented by formula (I) or (II) of the present invention forms an azomethine dye upon reaction with an oxidation product of an aromatic primary color developing agent.

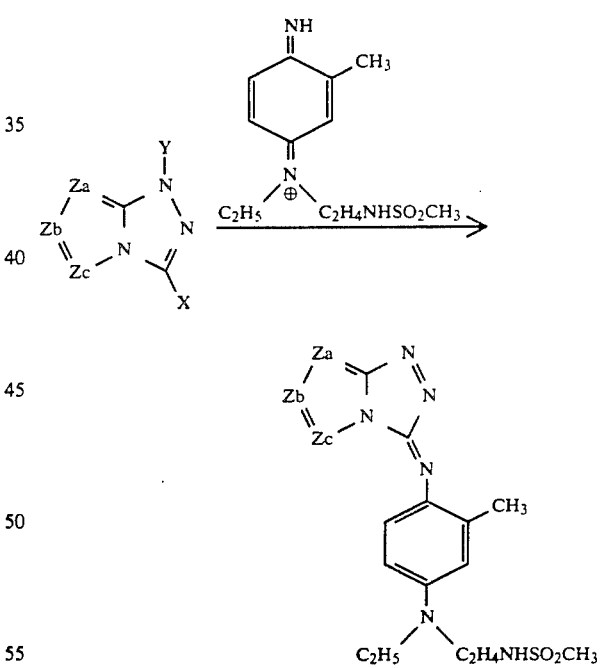

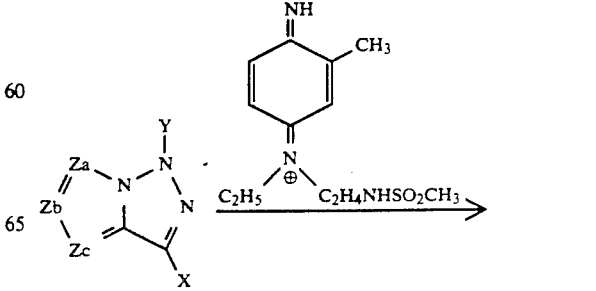

-continued

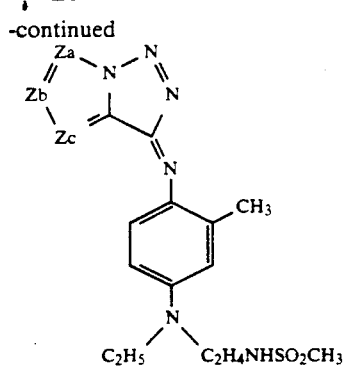

A standard amount of the cyan coupler to be used in the present invention is in the range of from 0.001 mol to 1 mol, preferably from 0.003 mol to 0.3 mol, per mol of light-sensitive silver halide present in the silver halide emulsion layer. When the cyan coupler is divided into plural layers, the amount is based on the total amount thereof.

The cyan coupler according to the present invention can be employed together with known yellow, magenta and cyan couplers.

Chemical structures of representative yellow couplers for use in the present invention include those described in U.S. Pat. Nos. 3,894,875 (columns 1 to 2), 3,408,194 (columns 2 to 3), 4,404,274 (columns 3 to 17), 4,022,620 (columns 3 to 7) and 4,057,432 (columns 1 to 4).

Chemical structure of representative magenta couplers for use in the present invention include those described in U.S. Pat. Nos. 3,519,429 (columns 2 to 6), 3,558,319 (columns 2 to 3), 3,725,067 (columns 2 to 8), 3,935,015 (columns 3 to 7), 4,241,168 (columns 2 to 14), 4,351,897 (columns 2 to 6), 4,367,282 (columns 3 to 10) and 4,540,654 (columns 2 to 8), JP-A-61-65245 (columns 378 to 384), and WO-86-1915 (columns 5 to 10).

Chemical structures of representative cyan couplers for use int he present invention include those described in U.S. Pat. Nos. 2,920,961 (column 1), 3,772,002 (columns 1 to 3), 3,864,366 (columns 2 to 6), 4,124,396 (column 2), 4,333,996 (columns 2 to 8), 4,565,777 (columns 3 to 5) and 4,564,586 (columns 2 to 4).

Chemical structures of representative yellow, magenta and cyan couplers for use with the couplers of the present invention are set forth below, but the present invention should not be construed as being limited thereto.

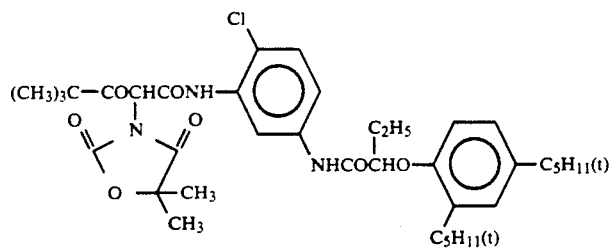

(Y-1)

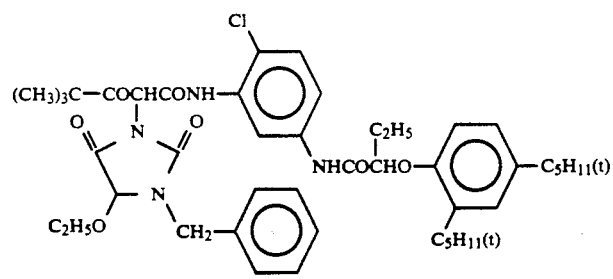

(Y-2)

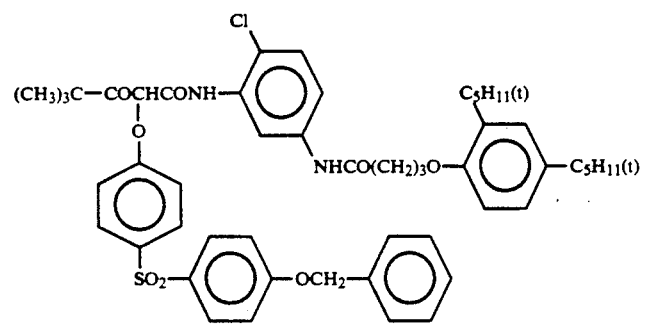

(Y-3)

-continued
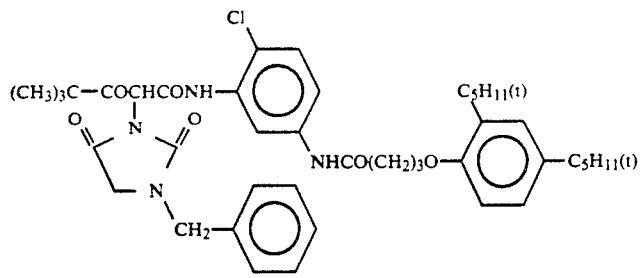
(Y-4)
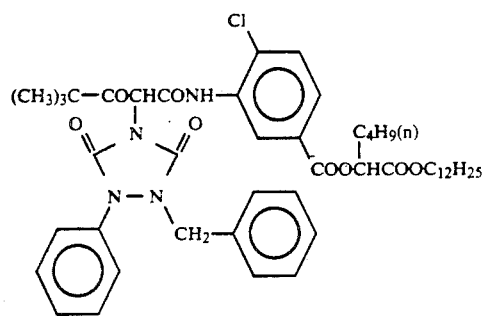
(Y-5)
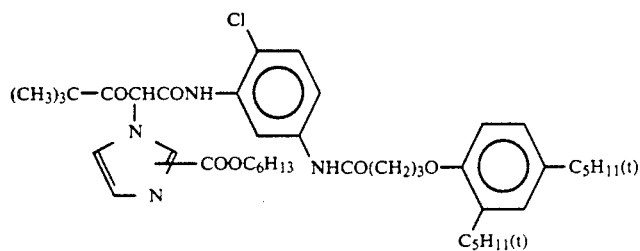
(Y-6)
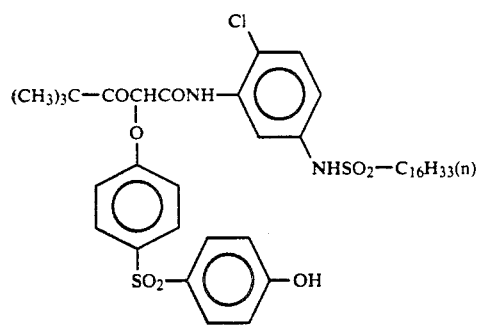
(Y-7)
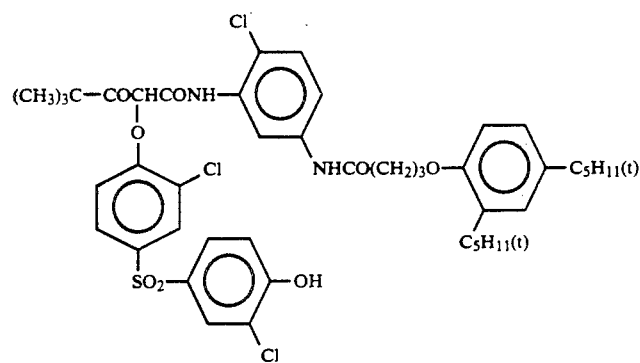
(Y-8)

-continued
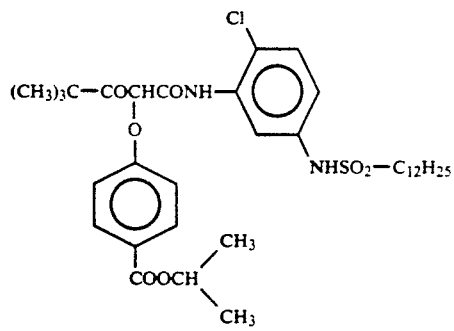 (Y-9)
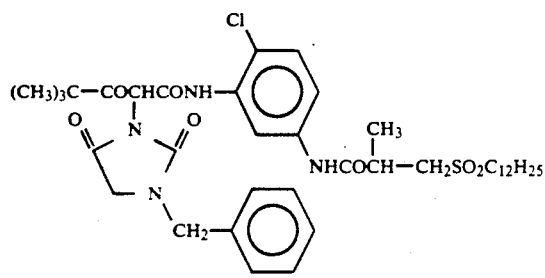 (Y-10)
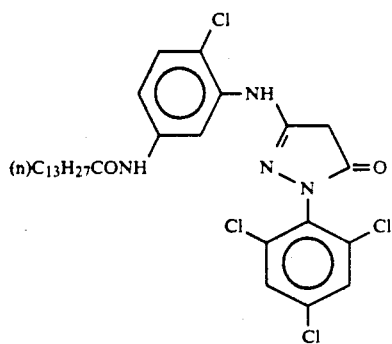 (M-1)
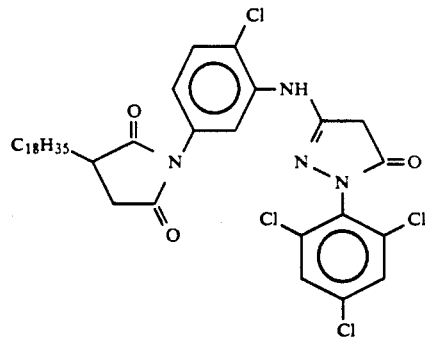 (M-2)
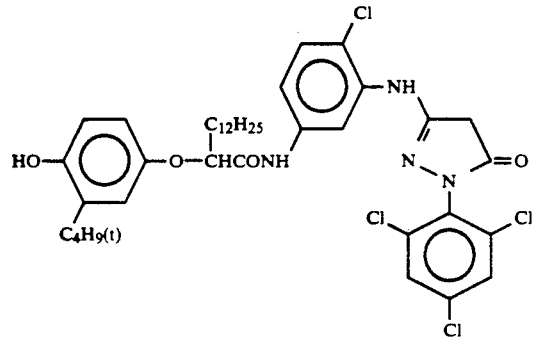 (M-3)

-continued
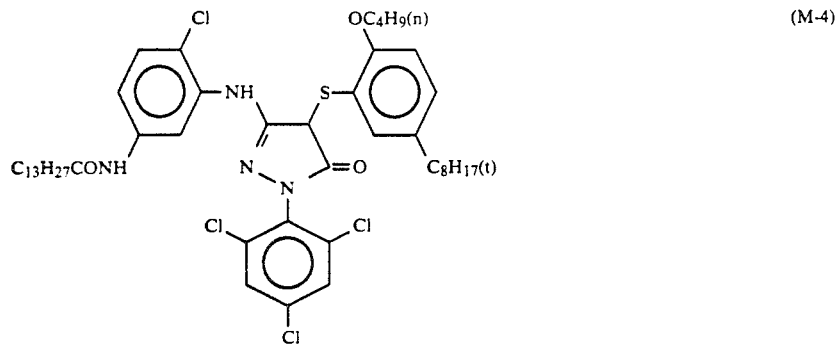 (M-4)
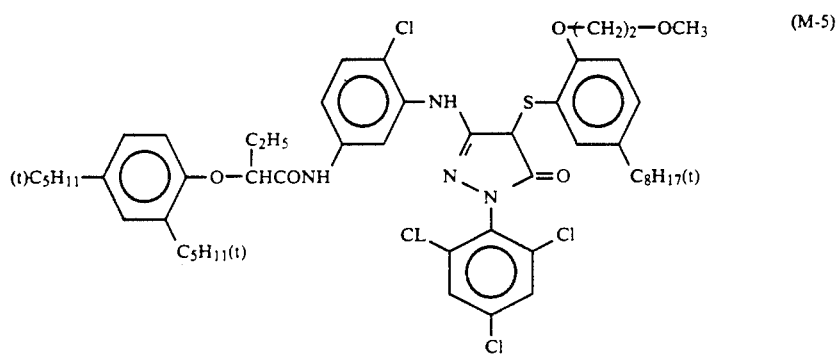 (M-5)
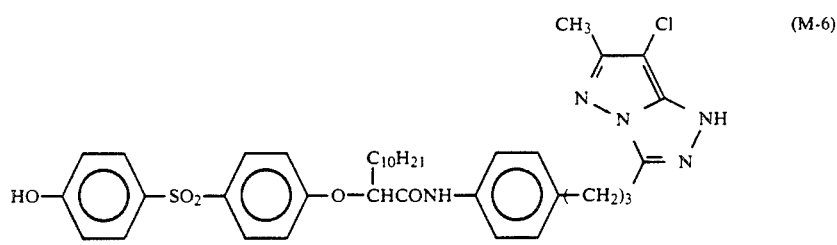 (M-6)
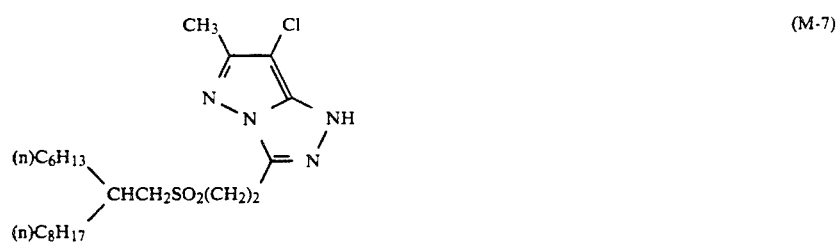 (M-7)
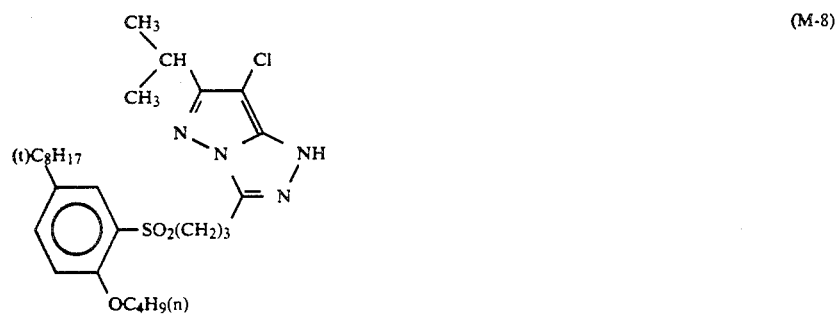 (M-8)

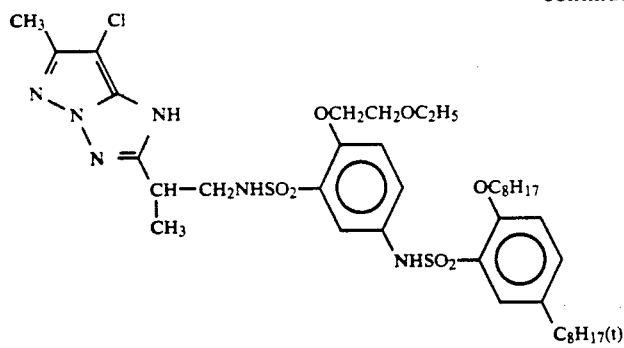
(M-9)
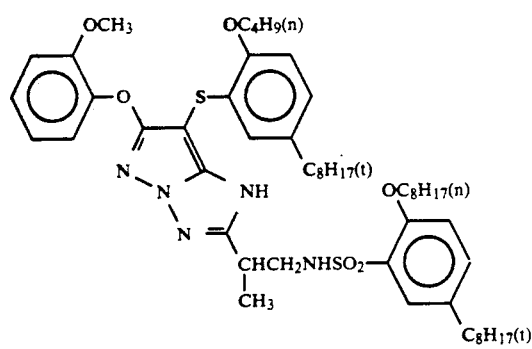
(M-10)
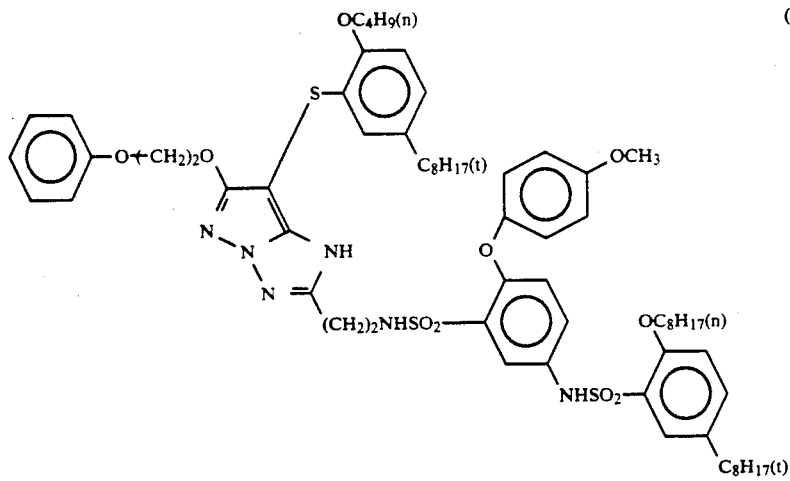
(M-11)
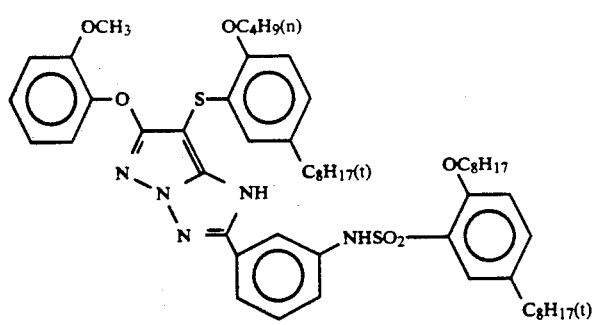
(M-12)
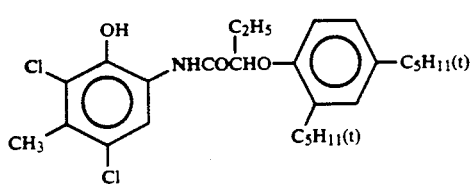
(C-1)

-continued
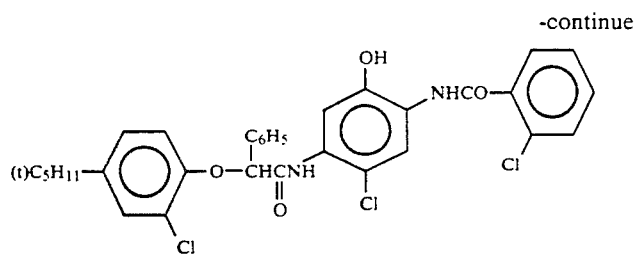 (C-2)
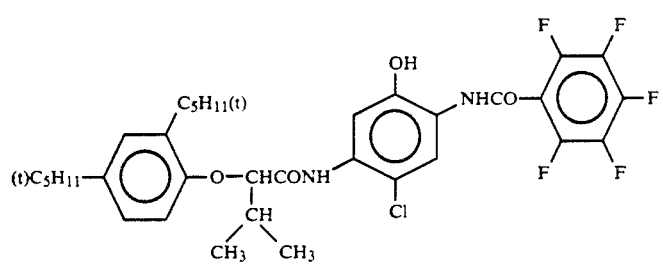 (C-3)
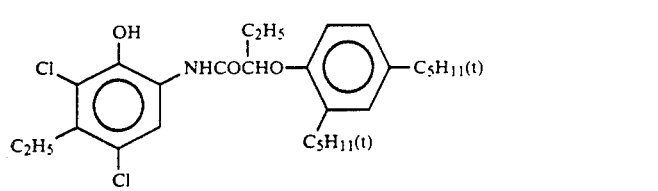 (C-4)
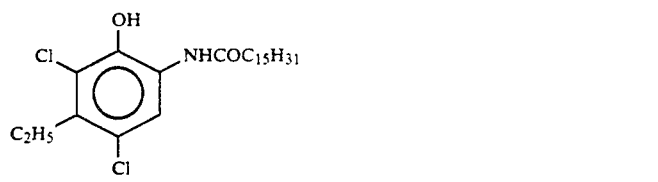 (C-5)
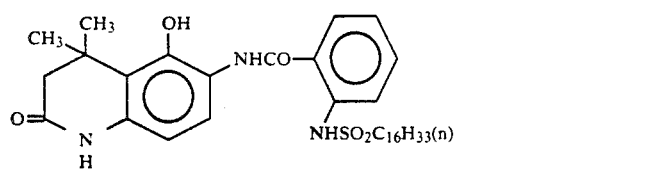 (C-6)
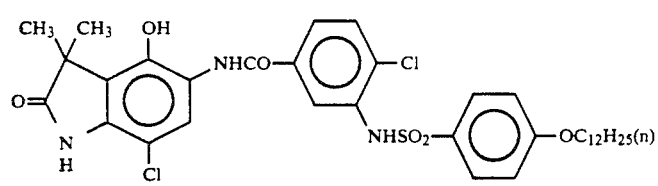 (C-7)
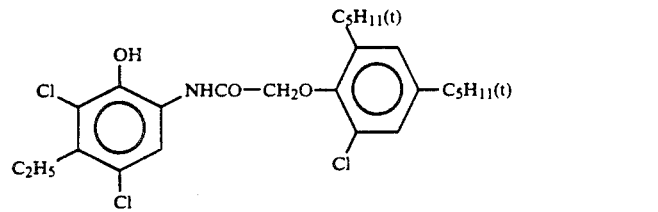 (C-8)
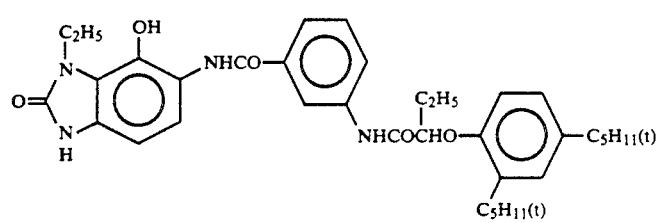 (C-9)

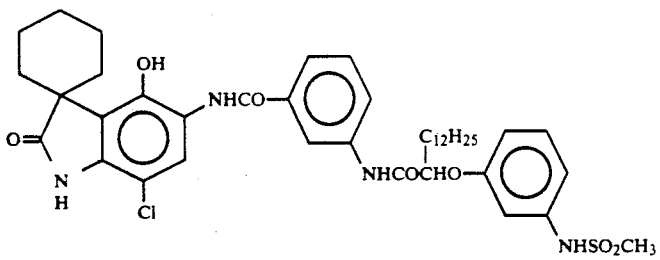
(C-10)

Known color fading preventing agent can be employed together with the cyan coupler of the present invention. These color fading preventing agents for use in the present invention include those described in U.S. Pat. Nos. 3,432,300, 3,573,045, 3,574,627, 3,700,455, 3,764,337, 3,935,016, 4,254,216, 4,268,593, 4,430,425, 4,465,757, 4,465,765 and 4,518,679, British Patent 1,347,556, British Patent No. 2,066,975A, JP-A-52-152225, JP-A-53-17729, JP-A-53-20327, JP-A-54-145530, JP-A-55-6321, JP-A-55-21004, JP-A-61-72246, JP-A-61-73152, JP-A-61-90155, JP-A-61-90156 and JP-A-61-145554.

Specific examples of representative color fading preventing agents for use in the present invention are set forth below, but the present invention should not be construed as being limited thereto.

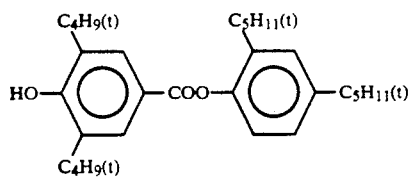
(T-1)

Mixture of benzotriazole compounds (T-2)

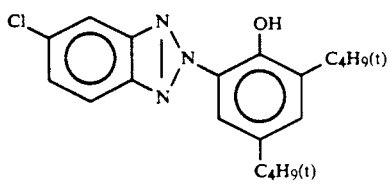 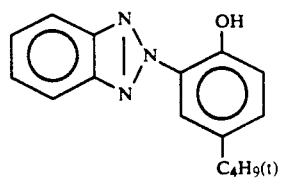

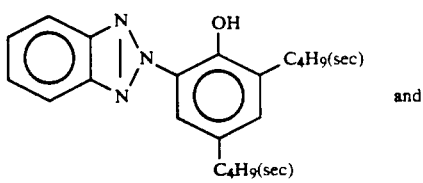 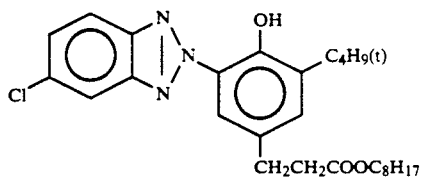

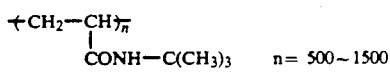
(T-3)

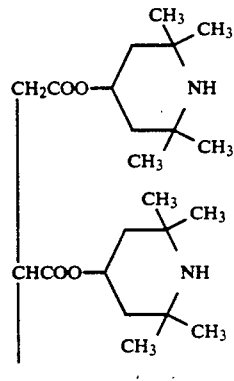
(T-4)

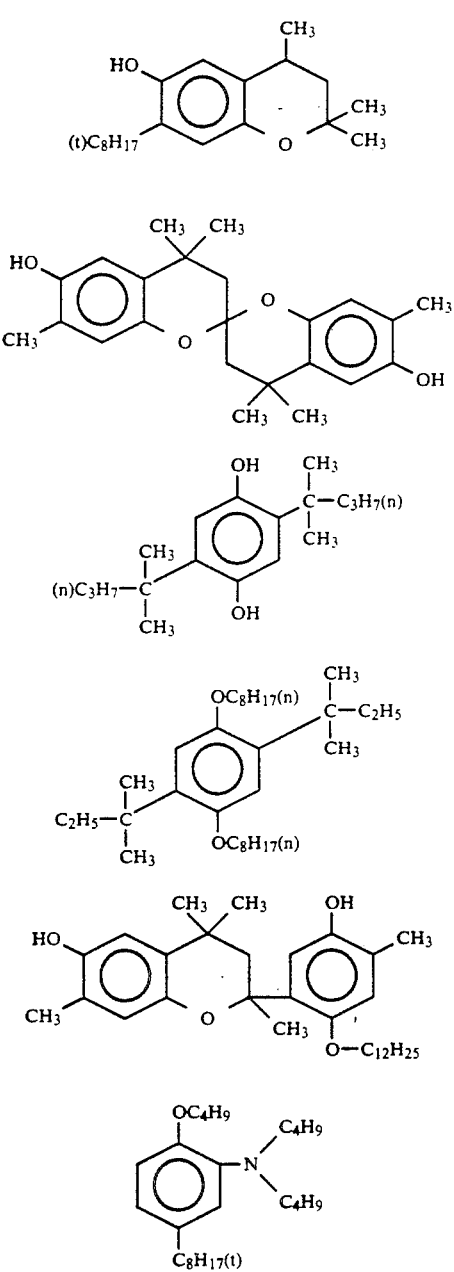
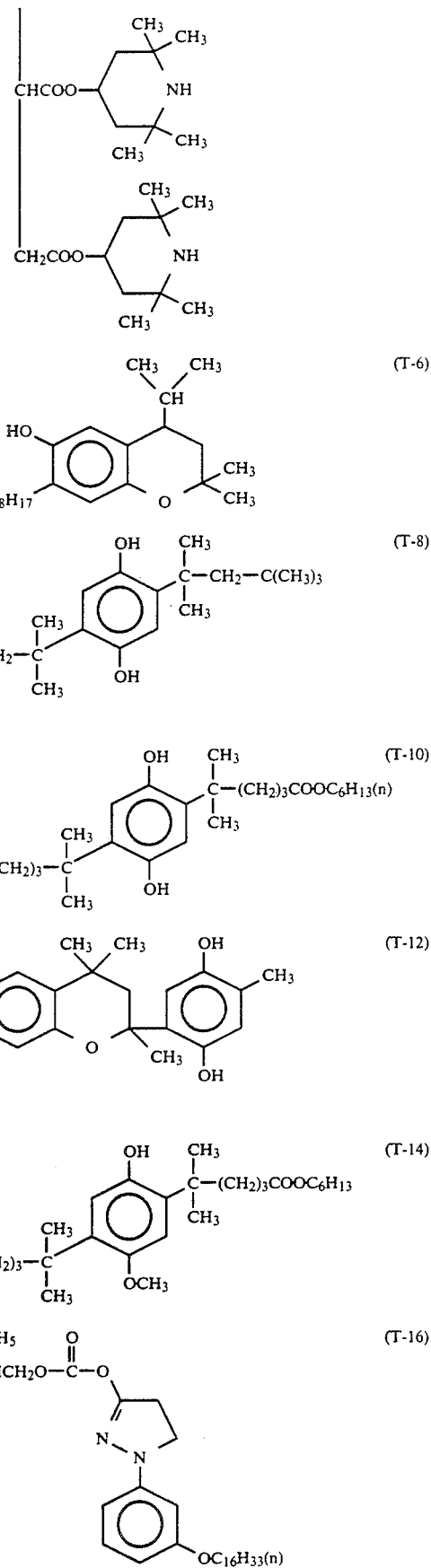

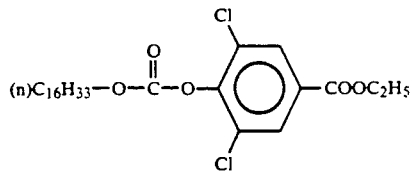
(T-17)

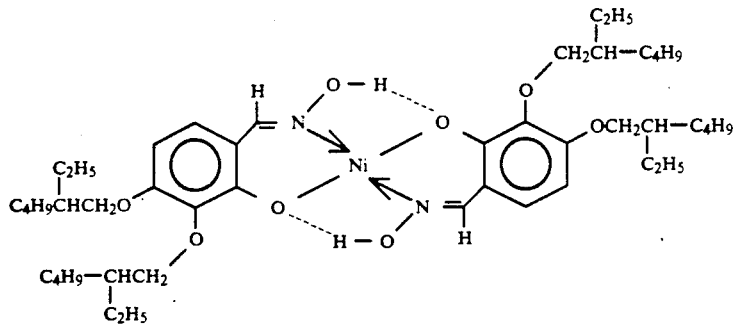
(T-18)

The color photographic light-sensitive material of the present invention may comprise in one embodiment at least one blue-sensitive silver halide emulsion layer, at least one green-sensitive silver halide emulsion layer and at least one red-sensitive silver halide emulsion layer on a support. The number of silver halide emulsion layers and light-insensitive layers and the positioned order thereof in relation to the support are not particularly restricted. A typical example is a silver halide photographic material comprising a support having thereon at least one light-sensitive layer unit group composed of a plurality of silver halide emulsion layers having substantially the same spectral sensitivity but different photographic speed. The light-sensitive unit layer may have a spectral sensitivity to any of blue light, green light and red light. In a multilayer silver halide color photographic material, unit light-sensitive layers are generally provided in the order of a red-sensitive layer, a green-sensitive layer and a blue-sensitive layer from the support side on the support. The order of these layers can be varied depending on the intended purpose of the photographic material. Further, a light-sensitive layer having a different spectral sensitivity may be provided between two layers having the same spectral sensitivity.

Various light-insensitive layers such as an intermediate layer can be provided between the above described silver halide light-sensitive layers or as the uppermost layer or the undermost layer.

Couplers and DIR compounds as described, for example, in JP-A-61-43748, JP-A-59-113438, JP-A-59-113440, JP-A-61-20037 and JP-A-61-20038 may be incorporated into such an intermediate layer. Further, the intermediate layer may contain conventional color mixing preventing agents.

The plurality of silver halide emulsion layers which constitute the unit light-sensitive layer preferably have a two layer construction consisting of a high speed emulsion layer and a low speed emulsion layer as described, for example, in West German Patent 1,121,470 and British Patent 923,045. It is preferred that these layers are disposed in order of increasing speed from the support side. Further, a light-insensitive layer may be provided between silver halide emulsion layers. Moreover, a low speed emulsion layer may be provided further away from the support and a high speed emulsion layer may be provided on the side closest to the support as described, for example, in JP-A-57-112751, JP-A-62-200350, JP-A-62-206541 and JP-A-62-206543.

Specific examples of the layer construction for use in the present invention include an order of a low speed blue-sensitive layer (BL)/ a high speed blue-sensitive layer (BH)/a high speed green-sensitive layer (GH)/a low speed green-sensitive layer (GL)/a high speed red-sensitive layer (RH)/a low speed red-sensitive layer (RL) from the furthest from the support, an order of BH/BL/GL/GH/ RH/RL, or an order of BH/BL/GH/GL/RL/RH.

Further, an order of a blue-sensitive layer/GH/RH/GL/RL from the furthest from the support as described in JP-B-55-34932 (the term "JP-B" as used herein means an "examined Japanese patent publication") may be employed. Moreover, an order of a blue-sensitive layer/GL/RL/GH/RH from the furthest support as described in JP-A-56-25738 and JP-A-62-63936 may also employed.

Furthermore, a layer construction of three layers having different speeds consisting of an upper silver halide emulsion layer having highest speed, an intermediate silver halide emulsion layer having lower speed than that of the upper layer, and an undermost silver halide emulsion layer having lower speed than that of the intermediate layer in order of increasing speed from the support side as described in JP B-49-15495 can also be employed in the present invention. When the unit light-sensitive layer of the same spectral sensitivity is composed of three layers having different speeds, an order of an intermediate speed emulsion layer/a high speed emulsion layer/a low speed emulsion layer from the furthest from the support may be employed as described in JP-A 59-202464.

As described above, various layer constructions and dispositions thereof may be appropriately selected depending on the purpose of the photographic light-sensitive material.

A silver halide to be used in the present invention includes silver bromide, silver iodobromide, silver iodochlorobromide, silver chlorobromide, and silver chloride. For rapid processing, it is preffered to use silver chlorobromide containing 90 mol % or more (preferably 98 mol % or more) of silver chloride. This silver chlorobromide may contain a slight amount of silver iodide, but it is more preferred to contain no silver iodide.

Silver halide grains in the silver halide emulsion of the present invention may have a regular crystal structure, for example, a cubic, octahedral or tetradecahedral structure, an irregular crystal structure, for example, a spherical or tabular structure, a crystal defect, for example, a twin plane, or a composite structure thereof.

A particle size of the silver halide emulsion of the present invention may vary and includes fine grains of about 0.2 micron or less to large size grains having about a 10 micron diameter of projected area. Further, a polydispersed emulsion and a monodispersed emulsion may be used.

The silver halide photographic emulsion for use in the present invention can be prepared using known methods, for example, as described in *Research Disclosure*, No. 17643 (December, 1978), pages 22 to 23, "I. Emulsion Preparation and Types" and ibid., No. 18716 (November, 1979), page 648, P. Glafkides, *Chimie et Physique Photographique*, Paul Montel (1967), G. F. Duffin, *Photographic Emulsion Chemistry*, The Focal Press (1966), and V. L. Zelikman et al., *Making and Coating Photographic Emulsion*, The Focal Press (1964).

Monodispersed emulsions as described, for example, in U.S. Pat. Nos. 3,574,628 and 3,655,394, and British Patent 1,413,748 are preferably used in the present invention.

Further, tabular silver halide grains having an aspect ratio of about 5 or more can be employed in the present invention. Tabular grains are easily prepared by the method as described, for example, in Gutoff, *Photographic Science and Engineering*, Vol. 14, pages 248 to 257 (1970), U.S. Pat. Nos. 4,434,226, 4,414,310, 4,433,048 and 4,439,520, and British Patent 2,112,157.

The crystal structure of silver halide grains for use in the present invention may be uniform, or be composed of different halide compositions between the inner portion and the outer portion thereof, or may have a stratified structure.

Further, silver halide emulsions wherein silver halide grains having different compositions are deposited upon epitaxial junctions or silver halide emulsions wherein silver halide grains are connected with compounds other than silver halide such as silver thiocyanate, or lead oxide may also be employed in the present invention.

Moreover, a mixture of grains having a different crystal structure may be used.

The silver halide emulsions for use in the present invention are usually prepared with physical ripening, chemical ripening and spectral sensitization. Various additives which can be employed in these steps are described in *Research Disclosure*, No. 17643, (December, 1978) and ibid., No. 18716 (November, 1979) and are summarized in the table below.

Further, other known photographic additives for use in the present invention also described in the above mentioned literatures are additionally summarized in the table below.

| Kind of Additives | RD 17643 | RD 18716 |
|---|---|---|
| 1. Chemical Sensitizers | Page 23 | Page 648, right column |
| 2. Sensitivity | | Page 648, |

-continued

| Kind of Additives | RD 17643 | RD 18716 |
|---|---|---|
| Increasing Agents | | right column |
| 3. Spectral Sensitizers and Supersensitizers | Pages 23 to 24 | Page 648, right column to page 649, right column |
| 4. Whitening Agents | Page 24 | |
| 5. Antifoggants and Stabilizers | Pages 24 to 25 | Page 649, right column |
| 6. Light-Absorbers, Filter Dyes and Ultraviolet Ray Absorbers | Pages 25 to 26 | Page 649, right column to page 650, left column |
| 7. Antistaining Agents | Page 25, right column | Page 650, left column to right column |
| 8. Dye Image Stabilizers | Page 25 | |
| 9. Hardeners | Page 26 | Page 651, left column |
| 10. Binders | Page 26 | Page 651, left column |
| 11. Plasticizers and Lubricants | Page 27 | Page 650, right column |
| 12. Coating Aids and Surfactants | Pages 26 to 27 | Page 650, right column |
| 13. Antistatic Agents | Page 27 | Page 650, right column |

Further, in order to prevent degradation of photographic properties in the presence of formaldehyde gas, a compound which fixes formaldehyde gas as described in U.S. Pat. Nos. 4,411,987 and 4,435,503 is preferably employed in the photographic light-sensitive material of the present invention.

In the present invention, various couplers as described below can be employed together with the cyan coupler according to the present invention and the yellow, magenta and other cyan couplers as described above.

Colored couplers for correcting undesirable side absorption of dyes formed upon development as described in *Research Disclosure*, No. 17643, "VII-G", U.S. Pat. No. 4,163,670, JP-B-57-39413, U.S. Pat. Nos. 4,004,929 and 4,138,258, and British Patent 1,146,368 are preferably employed.

Couplers capable of forming diffusible dyes as described in U.S. Pat. No. 4,366,237, British Patent 2,125,570, European Patent 96,570, and West German Patent Application (OLS) No. 3,234,533 are preferably employed.

Typical examples of polymerized dye forming couplers for use in the present invention are described in U.S. Pat. Nos. 3,451,820, 4,080,211, 4,367,282, 4,409,320 and 4,576,910, and British Patent 2,102,173.

Couplers capable of releasing a photographically useful moiety during the course of coupling can also be preferably employed in the present invention. The DIR couplers capable of releasing a development inhibitor as described in the patents cited in *Research Disclosure*, No. 17643, "VII-F" described above, JP-A-57-151944, JP-A-57-154234 and JP-A-60-184248, and U.S. Pat. No. 4,248,962 are preferred.

Couplers which imagewise release a nucleating agent or a development accelerator at the time of development can be employed in the present invention. Those described in British Patents 2,097,140 and 2,131,188, JP-A-59-157638, and JP-A-59-170840 are preferred.

Furthermore, competing couplers as described in U.S. Pat. No. 4,130,427; polyequivalent couplers as described in U.S. Pat. Nos. 4,283,472, 4,338,393 and 4,310,618; DIR redox compounds or DIR coupler releasing couplers or DIR coupler or DIR redox compound releasing redox compounds as described in JP-A-60-185950 and JP-A-62-24252; couplers capable of releasing a dye which turns to a colored form after being released as described in European Patent 173,302A; bleach accelerating agent releasing couplers as described in *Research Disclosure* Nos. 11449 and 24241 and JP-A-61-201247; and ligand releasing couplers as described in U.S. Pat. No. 4,553,477 may be employed in the photographic light-sensitive material of the present invention.

The couplers for use in the present invention can be introduced into the photographic light-sensitive material by various known dispersing methods.

Suitable examples of organic solvent having a high boiling point and which can be employed in an oil droplet-in-water type dispersing method are described, for example, in U.S. Pat. No. 2,322,027.

Specific examples of the organic solvents having a high boiling point of not less than 175° C. at normal pressure and which can be employed in the oil droplet-in-water type dispersing method include phthalic acid esters (for example, dibutyl phthalate, dicyclohexyl phthalate, di-2-ethylhexyl phthalate, didecyl phthalate, bis(2,4-di-tert-amylphenyl) phthalate, bis(2,4-di-tert-amylphenyl) isophthalate, or bis(1,1-diethylpropyl) phthalate, phosphoric acid or phosphonic acid esters (for example, triphenyl phosphate, tricresyl phosphate, 2-ethylhexyl diphenyl phosphate, tricyclohexyl phosphate, tri-2-ethylhexyl phosphate, tridodecyl phosphate, tributoxyethyl phosphate, trichloropropyl phosphate, or di-2-ethylhexyl phenyl phosphonate), benzoic acid esters (for example, 2-ethylhexyl benzoate, dodecyl benzoate, or 2-ethylhexyl-p-hydroxybenzoate), amides (for example, N,N-diethyldodecanamide, N,N-diethyllaurylamide, or N-tetradecylpyrrolidone), alcohols or phenols (for example, isostearyl alchol, or 2,4-di-tert-amylphenol), aliphatic carboxylic acid esters (for example, bis(2-ethylhexyl) sebacate, dioctyl azelate, glycerol tributyrate, isostearyl lactate, or trioctyl citrate), aniline derivatives (for example, N,N-dibutyl-2-butoxy-5-tert-octylaniline), and hydrocarbons (for example, paraffin, dodecylbenzene, or diisopropylnaphthalene).

Further, an organic solvent having a boiling point of at least about 30° C. and preferably above 50° C. but below about 160° C. can be used as an auxiliary solvent. Typical examples of auxiliary solvents include ethyl acetate, butyl acetate, ethyl propionate, methyl ethyl ketone, cyclohexanone, 2-ethoxyethyl acetate, or dimethylformamide.

The processes and effects of latex dispersing methods and specific examples of latexes useful for loading are described, for example, in U.S. Pat. No. 4,199,363, West German Patent Application (OLS) Nos. 2,541,274 and 2,541,230.

The present invention can be applied to various color photographic light-sensitive materials, and typical examples thereof include color negative films for general use or cinematography, color reversal films for slides or television, color papers, color positive films, and color reversal papers.

Suitable supports for use in the present invention are described, for example, in *Research Disclosure*, No. 17643, page 28 and ibid., No. 18716, page 647, right column to page 648, left column.

The color photographic light-sensitive material of the present invention can be subjected to development processing in a conventional manner as described in *Research Disclosure*, No. 17643, pages 28 to 29 and ibid., No. 18716, page 651, left column to right column.

A color developing solution for be use in the development processing of the color photographic light-sensitive material of the present invention is an alkaline aqueous solution containing preferably an aromatic primary amine type color developing agent as a main component. As the color developing agent, while an aminophenol type compound is useful, a p-phenylenediamine type compound is preferably employed. Typical examples of the p-phenylenediamine type compounds include 3-methyl-4-amino-N,N-diethylaniline, 3-methyl-4-amino-N-ethyl-N-$\beta$-hydroxyethylaniline, 3-methyl-4-amino-N-ethyl-N-$\beta$-methanesulfonamidoethylaniline, 3-methyl-4-amino-N-ethyl-N-$\beta$-methoxyethylaniline, or sulfate, hydrochloride or p-toluenesulfonate salt thereof.

Two or more kinds of color developing agents may be employed in a combination thereof, depending on the purpose, for the color development precessing of the photographic material of the present invention.

The color developing solution can ordinarily contain pH buffering agents, such as carbonates, borates or phosphates of alkali metals; and development inhibitors or anti-fogging agents such as bromides, iodides, benzimidazoles, benzothiazoles, or mercapto compounds. Further, if necessary, the color developing solution may contain various preservatives such as hydroxylamine, diethylhydroxylamine, sulfites, hydrazines, phenyl semicarbazides, triethanolamine, catechol sulfonic acids, or triethylenediamine(1,4-diazabicyclo[2,2,2]octane); organic solvents such as ethyleneglycol, or diethylene glycol; development accelerators such as benzyl alcohol, polyethylene glycol, quarternary ammonium salts, or amines; dye forming couplers; competing couplers; fogging agents such as sodium borohydride; auxiliary developing agents such as 1-phenyl-3-pyrazolidone; viscosity imparting agents; and various chelating agents represented by the aminopolycarboxylic acids, aminopolyphosphonic acids, alkylphosphonic acids, or phosphonocarboxylic acids. Representative examples of the chelating agents include ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N',N'-tetramethylenephosphonic acid, ethylenediamine-di(o-hydroxyphenylacetic acid), and salts thereof.

For reversal processing, color development is usually conducted following black-and-white development. In a black-and-white developing solution, known black-and-white developing agents, for example, dihydroxybenzenes such as hydroquinone, 3-pyrazolidones such as 1-pheyl-3-pyrazolidone, or aminophenols such as N-methyl-p-aminophenol may be employed individually or in combination thereof.

The pH of the color developing solution or the black-and-white developing solution is usually in the range of from 9 to 12. Further, an amount of replenishment for the developing solution can vary depending on the color photographic light-sensitive materials to be processed, but is generally not more than 3 liters per square meter of the photographic light-sensitive material. The amount of replenishment can be reduced to not more than 500 ml by decreasing the bromide ion concentration in the replenisher. When reducing the amount of replenishment, it is preferred to prevent evaporation and aerial oxidation of the processing solution by means of reducing the area of the processing tank which is contact with the air. Further, the amount of replenishment can be reduced b restraining the accumulation of bromide ion in the developing solution.

The processing time for color development of the color photographic material of the present invention is usually selected in the range of from 2 minutes to 5 minutes. However, it is possible to reduce the processing time by performing the color development at a higher temperature and at a higher pH using a high or concentration of the color developing agent.

After color development, the photographic emulsion layers are usually bleach processed. The bleach processing can be performed simultaneously with a fix processing (bleach-fix processing), or it can be performed independently from the fix processing. Further, for rapid processing, a bleach-fix processing may be employed following the bleach processing. Moreover, a continuous two tank bleach-fixing bath may be used to carry out fix processing before bleach-fix processing, or to conduct bleach processing after bleach-fix processing.

Examples of bleaching agents which can be employed in the bleach processing or bleach-fix processing of the color photographic material of the present invention include compounds of a multivalent metal such as iron(III), cobalt(III), chromium(VI), or copper(II); peracids; quinones; or nitro compounds. Representative examples of the bleaching agents include ferricyanides; dichromates; organic complex salts of iron(III) or cobalt(III), for example, complex salts of aminopolycarboxylic acids (such as ethylenediaminetetraacetic acid, diethylenetriaminepentaacetic acid, cyclohexanediaminetetraacetic acid, methyliminodiacetic acid, 1,3-diaminopropanetetraacetic acid, or glycol ether diaminetetraacetic acid), or complex salts of organic acids (such as citric acid, tartaric acid, or malic acid); persulfates; bromates; permanganates; or nitrobenzenes. Of these compounds, iron(III) complex salts of aminopolycarboxylic acids represented by the iron(III) complex salt of ethylenediaminetetraacetic acid and persulfates are preferred in view of rapid processing and environmental factors. Furthermore, iron(III) complex salts of aminopolycarboxylic acids are particularly useful in both bleaching solutions and bleach-fixing solutions.

The pH of the bleaching solution or bleach-fixing solution containing an iron(III) complex salt of aminopolycarboxylic acid is usually adjusted in a range of from 5.5 to 8. For the purpose of rapid processing, it is possible to process at pH lower than the above described range.

In the bleaching solution, the bleach-fixing solution or a prebath thereof, a bleach accelerating agent can be used, if desired. Specific examples of suitable bleach accelerating agents include compounds having a mercapto group or a disulfide bond as described, for example, in U.S. Pat. No. 3,893,858, West German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426, and Research Disclosure, No. 17129 (July 1978); thiazolidine derivatives as described, for example, in JP-A-50-140129; thiourea derivatives as described, for example, in JP-B-45-8506, JP-A-52-20832, JP-A-53-32735 and U.S. Pat. No. 3,706,561; iodides as described, for example, in West German Patent 1,127,715 and JP-A-58-16235; polyoxyethylene compounds as described, for example, in West German Patents 966,410 and 2,748,430; polyamine compounds as described, for example, in JP-B-45-8836; compounds as described, for example, in JP-A-49-42434, JP-A-49-59644, JP-A-53-94927, JP-A-54-35727, JP-A-55-26506, and JP-A-58-163940; and bromide ions. Of these compounds, the compounds having a mercapto group or a disulfide bond are preferred in view of their large bleach accelerating effects. In particular, the compounds as described in U.S. Pat. No. 3,893,858, West German Patent 1,290,812 and JP-A-53-95630 are preferred. Further, the compounds as described in U.S. Pat. No. 4,552,834 are also preferred. These bleach accelerating agents may also be incorporated into the color photographic light-sensitive material. These bleach accelerating agents are particularly effectively employed when color photographic light sensitive materials for photographing are subjected to bleach-fix processing.

Fixing agents which can be employed in the fixing solution or bleach-fixing solution include thiosulfates, thiocyanate, thioether compounds, thioureas, or a large amount of iodide. Of these compounds, thiosulfates are generally employed. In particular, ammonium thiosulfate is most widely employed. Sulfites, bisulfites or carbonylbisulfite adducts are preferably used as preservatives in the bleach-fixing solution.

After a desilvering step, the silver halide color photographic material of the present invention is generally subjected to a water washing step and/or a stabilizing step.

The amount of water required for the water washing step is set depending on the characteristics of the photographic light-sensitive materials (the composition thereof, for example, couplers, etc.), uses thereof, temperature of the washing water, the number of water washing tanks (stages) employed, the type of replenishment system employed (e.g., countercurrent or orderly current), or other various conditions. The relationship between the number of water washing tanks and the amount of water to be used in a multi-stage countercurrent system can be determined based on the method described in *Journal of the Society of Motion Picture and Television Engineers*, Vol. 64, pages 248 to 253 (May, 1955).

According to the multi-stage countercurrent system described in the above literature, the amount of water for washing can be significantly reduced. However, the increase in residence time of water in a tank causes the propagation of bacteria and other problems such as adhesion of floatage thus formed in the tank on the photographic materials. In the method of processing the silver halide color photographic material of the present invention, a method for reducing the amount of calcium ion and magnesium ion as described in JP-A-62-288838 can be effectively employed in order to solve such problems. Further, sterilizers, for example, isothiazolone compounds as described in JP-A-57-8542, thiabendazoles, chlorine type sterilizers such as sodium chloroisocyanurate, benzotriazoles, sterilizers as described in Hiroshi Horiguchi, *Bokin-Bobai No Kaqaku, Biseibutsu No Mekkin-, Sakkin-, Bobai-Gijutsu*, edited by Eiseigijutsu Kai, and *Bokin-Bobaizai Jiten*, edited by Nippon Bokin-Bobai Gakkai can also be employed.

The pH of the washing water used in the processing of the photographic light-sensitive material of the present invention ranges from 4 to 9, and preferably from 5 to 8. The temperature of the washing water and the water washing time can be varied depending on the characteristics or intended use of the photographic light-sensitive materials. However, it is generally desirable to select a range of from 15° C. to 45° C. and a period from 20 sec. to 10 min. and a range of from 25° C. to 40° C. and a period from 30 sec. to 5 min is preferred.

The photographic light-sensitive material of the present invention can also be directly processed with a stabilizing solution in place of the above-described water washing step. In such a stabilizing process, any of known methods as described, for example, in JP-A-57-8543, JP-A-58-14834 and JP-A-60-220345 ca be employed.

Further, it is possible to conduct the stabilizing process subsequent to the above-described water washing process. One example thereof is a stabilizing bath containing formalin and a surface active agent, which is employed as a final bath in the processing of color photographic light-sensitive materials for photographing. To such a stabilizing bath, various chelating agents and antimold agents may also be added.

Overflow solutions resulting from replenishment for the above-described washing water and/or stabilizing solution may be reused in other steps such as a desilvering step.

For the purpose of simplification and acceleration of processing, a color developing agent may be incorporated into the silver halide color photographic material of the present invention. The color developing agent is preferably incorporated as a precursor thereof. Suitable examples of developing agent precursors include indoaniline type compounds as described in U.S. Pat. No. 3,342,597, Schiff's base type compounds as described in U.S. Pat. No. 3,342,599 and Research Disclosure, No. 14850 and ibid., No. 15159, aldol compounds as described in Research Disclosure, No. 13924, metal salt complexes as described in U.S. Pat. No. 3,719,492, and urethane type compounds as described in JP-A-53-135628.

Further, the silver halide color photographic material of the present invention may contain, if desired, various 1-phenyl-3-pyrazolidones for the purpose of accelerating color development. Typical examples of these compounds are described, for example, in JP-A-56-64339, JP-A-57-144547, and JP-A-58-115438.

In processing the photographic material of the present invention, various kinds of processing solutions can be employed in a temperature range of from 10° C. to 50° C. Although a standard temperature range is from 33° C. to 38° C., it is possible to carry out the processing at higher temperatures in order to accelerate the processing in order to shorten the processing time, or at lower temperatures in order to improve image quality and to maintain stability of the processing solutions Further, for the purpose of reducing the amount of silver to be employed in the color photographic light-sensitive material of the present invention, the photographic processing may be conducted utilizing color intensification using cobalt or hydrogen peroxide as described in West German Patent 2,226,770 or U.S. Pat. No. 3,674,499.

Moreover, the silver halide color photographic material of the present invention can be applied to heat-developable light-sensitive materials as described, for example, in U.S. Pat. No. 4,500,626, JP-A-60-133449, JP-A-59-218443, JP-A-61-238056 and European Patent 210,660A2.

In accordance with the present invention, color images excellent in color reproducibility of blue and green and in image preservability are obtained.

The present invention will now be explained in greater detail with reference to the following examples, but the present invention should not be construed as being limited thereto.

EXAMPLE 1

On a paper support, both surfaces of which were laminated with polyethylene, layers were coated as described below to prepare a multilayer color photographic light-sensitive material designated Light-Sensitive Material 1-1. The coating solutions were prepared in the following manner.

Preparation of the Coating Solution for the First Layer:

19.1 g of Yellow coupler (ExY-1), 1.91 g of dispersion Polymer (Cpd-1) and 0.46 g of Antifogging agent (Cpd-2) were dissolved in a mixture of 27.2 ml of ethyl acetate, 3.8 ml of Solvent (Solv-1) and 3.8 ml of Solvent (Solv 2). The resulting solution was emulsified and dispersed in 185 ml of a 10% aqueous solution of gelatin containing 8 ml of a 10% aqueous solution of sodium dodecylbenzenesulfonate. Separately, to a silver chlorobromide emulsion (having a bromide content of 80.0 mol % and containing 70 g of silver per kg of the emulsion), $5.0 \times 10^{-4}$ mols of a blue-sensitive sensitizing dye shown below was added per mol of silver to prepare a blue-sensitive emulsion. The above described emulsified dispersion was mixed with the blue-sensitive silver chlorobromide emulsion, with the concentration of the resulting mixture being controlled, to form the composition as shown below, i.e., the coating solution for the first layer.

Coating solutions for the second layer to the seventh layer were prepared in a similar manner as described for the coating solution for the first layer.

2-Oxy-4, 6-dichloro-s-triazine sodium salt was used as a gelatin hardener in each layer.

The following spectral sensitizing dyes were employed in the emulsion layers, respectively.

Blue-Sensitive Emulsion Layer:

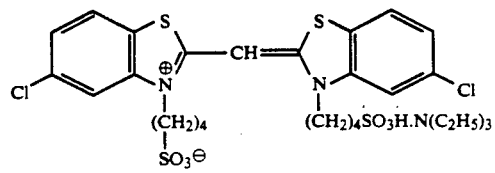

(Amount added: $5.0 \times 10^{-4}$ mol per mol of silver halide)

Green-Sensitive Emulsion Layer:

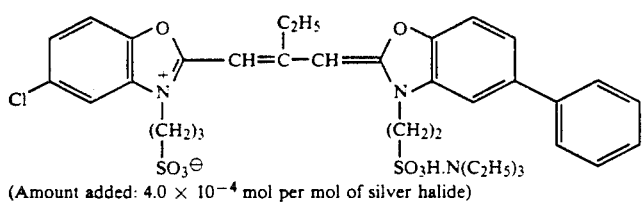

(Amount added: 4.0 × 10⁻⁴ mol per mol of silver halide)

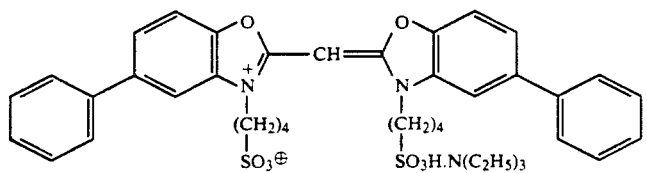

(Amount added: 7.0 × 10⁻⁵ mol per mol of silver halide)

Red-Sensitive Emulsion Layer:

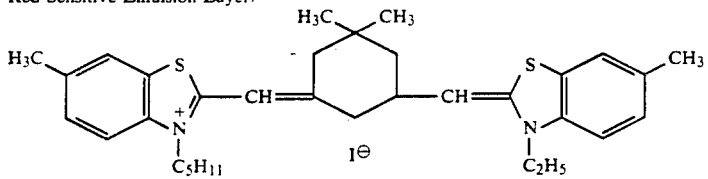

(Amount added: 0.9 × 10⁻⁴ mol per mol of silver halide)

To the red-sensitive emulsion layer, the compound shown below was added in an amount of $2.6 \times 10^{-3}$ mol per mol of silver halide.

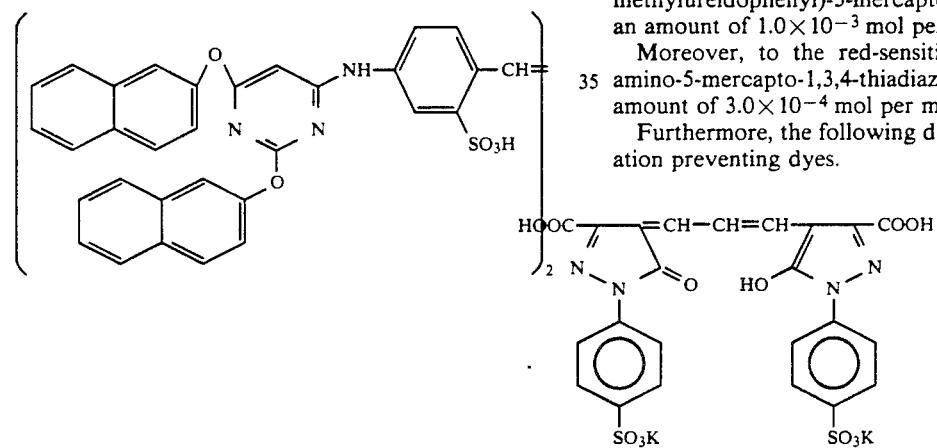

To the blue-sensitive emulsion layer and green-sensitive emulsion layer, 4-hydroxy-6-methyl-1,3,3a,7-tetraazaindene was added in amounts of $1.2 \times 10^{-2}$ mol and $1.1 \times 10^{-2}$ mol per mol of silver halide, respectively.

Further, to the green-sensitive emulsion layer, 1-(5-methylureidophenyl)-5-mercaptotetrazole was added in an amount of $1.0 \times 10^{-3}$ mol per mol of silver halide.

Moreover, to the red-sensitive emulsion layer, 2-amino-5-mercapto-1,3,4-thiadiazole was added in an amount of $3.0 \times 10^{-4}$ mol per mol of silver halide.

Furthermore, the following dyes were used as irradiation preventing dyes.

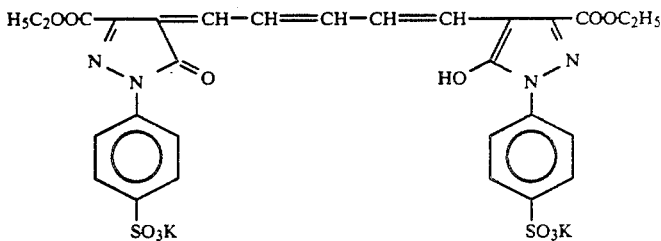

and

Layer Construction

The composition of each layer is shown below. The numerical value denotes the coating amounts in the unit of g/m². The coating amount of silver halide emulsion is indicated in terms of the silver coating amount.

| Support | Paper support, both surfaces of which were laminated with polyethylene (the polyethylene coating containing a white pigment (TiO₂) and a bluish dye (ultramarine) on the first layer side) | |
|---|---|---|
| First Layer (Blue-sensitive layer) | Silver chlorobromide emulsion (Br: 80 mol %) | 0.26 |
| | Gelatin | 1.20 |
| | Yellow Coupler (ExY-1) | 0.66 |
| | Polymer for dispersion (Cpd-1) | 0.07 |
| | Antifogging agent (Cpd-2) | 0.02 |
| | Solvent (Solv-1) | 0.13 |
| | Solvent (Solv-2) | 0.13 |
| Second Layer (Color mixing preventing layer) | Gelatin | 1.34 |
| | Color mixing preventing agent (Cpd-3) | 0.04 |
| | Solvent (Solv-3) | 0.10 |
| | Solvent (Solv-4) | 0.10 |
| Third Layer (Green-sensitive layer) | Silver chlorobromide emulsion (Br: 80 mol %) | 0.14 |
| | Gelatin | 1.30 |
| | Magenta coupler (ExM-1) | 0.27 |
| | Color image stabilizer (Cpd-4) | 0.16 |
| | Color image stabilizer (Cpd-5) | 0.025 |
| | Color image stabilizer (Cpd-6) | 0.032 |
| | Solvent (Solv-3) | 0.21 |

| | | |
|---|---|---|
| | Solvent (Solv-5) | 0.33 |
| Fourth Layer (Ultraviolet light absorbing layer) | Gelatin | 1.44 |
| | Ultraviolet light absorbing agent (UV-1) | 0.53 |
| | Color mixing preventing agent (Cpd-3) | 0.05 |
| | Solvent (Solv-6) | 0.26 |
| Fifth Layer (Red-sensitive layer) | Silver chlorobromide emulsion (Br: 70 mol %) | 0.20 |
| | Gelatin | 0.89 |
| | Cyan coupler (ExC-1) | 0.40 |
| | Color image stabilizer (Cpd-5) | 0.004 |
| | Color image stabilizer (Cpd-6) | 0.007 |
| | Polymer for dispersion (Cpd-1) | 0.20 |
| | Color image stabilizer (Cpd-7) | 0.07 |
| | Antifogging agent (Cpd-2) | 0.01 |
| | Solvent (Solv-1) | 0.19 |
| Sixth Layer (Ultraviolet light absorbing layer) | Gelatin | 0.47 |
| | Ultraviolet light absorbing agent (UV-1) | 0.17 |
| | Solvent (Solv-2) | 0.08 |
| Seventh Layer (Protective layer) | Gelatin | 1.25 |
| | Acryl-modified polyvinyl alcohol copolymer (Degree of modification: 17%) | 0.05 |
| | Liquid paraffin | 0.02 |

The compounds used in the above-described layers have the structures shown below respectively.

Yellow coupler (ExY-1)

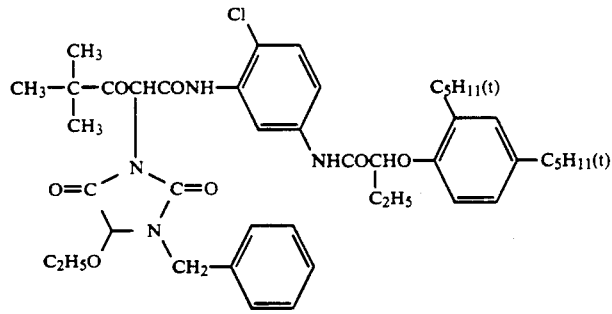

Magenta coupler (ExM-1)

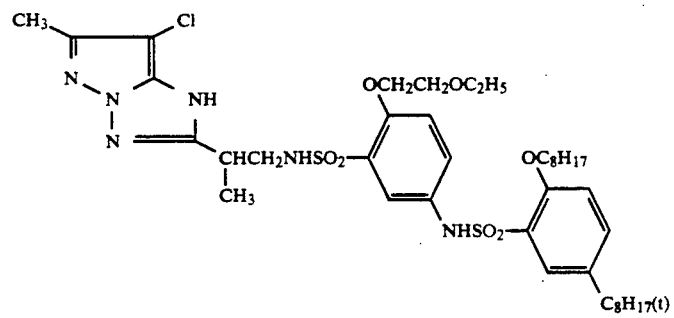

Cyan coupler (ExC-1) (corresponding to Compound (19))

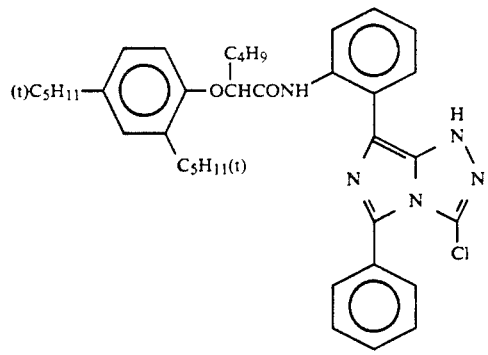
Polymer for dispersion (Cpd-1)
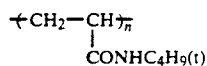
(average molecular weight: 60,000)
Antifogging agent (Cpd-2)
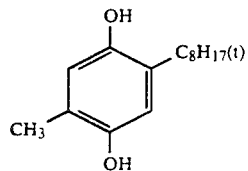
Color mixing preventing agent (Cpd-3)
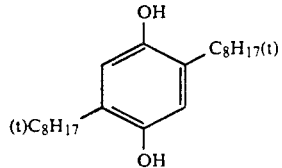
Color image stabilizer (Cpd-4)
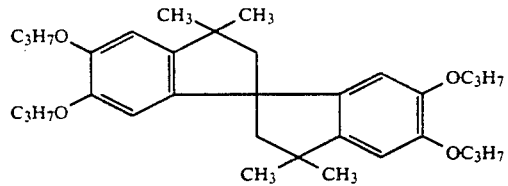
Color image stabilizer (Cpd-5)
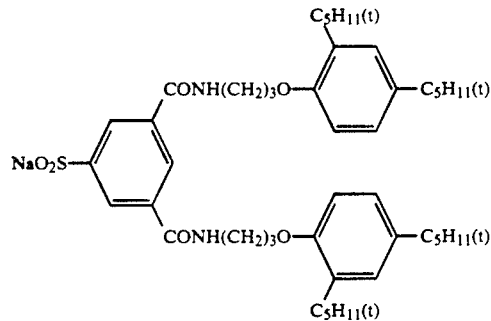
Color image stabilizer (Cpd-6)

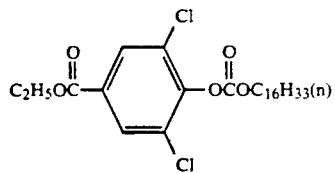
Color image stabilizer (Cpd-7)
A mixture of
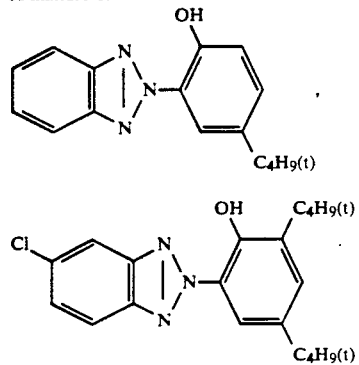
and
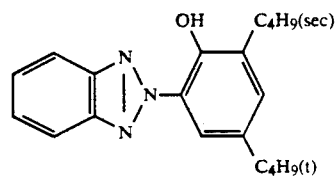
in a weight ratio of 4:2:5.
Ultraviolet light absorbing agent (UV-1)
A mixture of
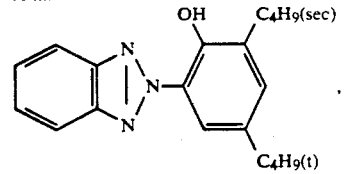
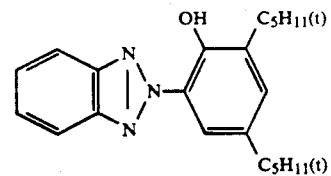
and
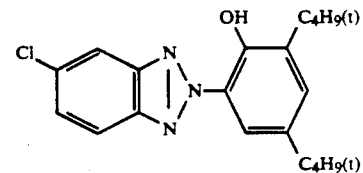
in a weight ratio of 12:10:3.
Solvent (Solv-1)
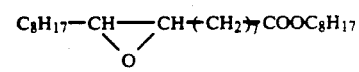

Solvent (Solv-2)

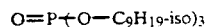

Solvent (Solv-3)

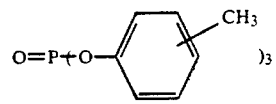

Solvent (Solv-4)

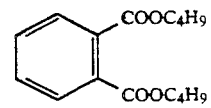

Solvent (Solv-5)

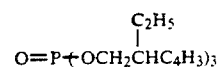

Solvent (Solv-6)

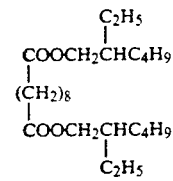

Light-Sensitive Materials 1-2 to 1-8 were prepared in the same manner as described for Light-Sensitive Material 1-1 except for using equimolar amounts of the cyan couplers described in Table 1 below in place of the cyan coupler employed in Light-Sensitive Material 1-1, respectively.

TABLE 1

| Light-Sensitive Material | Cyan Coupler | Remark |
|---|---|---|
| 1-1 | 19 | Present Invention |
| 1-2 | 21 | " |
| 1-3 | 24 | " |
| 1-4 | 30 | " |
| 1-5 | 36 | " |
| 1-6 | 41 | " |
| 1-7 | Comparative Compound A | Comparison |
| 108 | Comparative Compound B | " |

Comparative Compound A

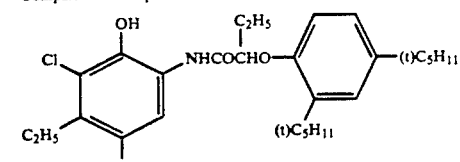

Compound B (described in European Patent 249,453)

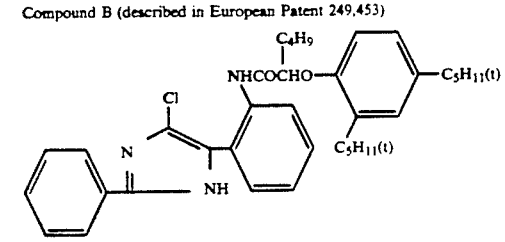

Light-Sensitive Materials 1-1 to 1-8 thus prepared were printed from a color negative film (Super HR 100 manufactured by Fuji Photo Film Co., Ltd.) having color negative images suitable for evaluating the resulting prints 1-1 to 1-8. The prints were then developed according to the following processing steps.

| Processing Step | Temperature (°C.) | Time |
|---|---|---|
| Color Development | 38 | 1 min. 40 sec. |
| Bleach-Fixing | 35 | 60 sec. |
| Rinse (1) | 33 to 35 | 20 sec. |
| Rinse (2) | 33 to 35 | 20 sec. |
| Rinse (3) | 33 to 35 | 20 sec. |
| Drying | 70 to 80 | 50 sec. |

The composition of each processing solution used was as follows:

| Color Developing Solution | |
|---|---|
| Water | 800 ml |
| Diethylenetriaminepentaacetic acid | 1.0 g |
| Nitrotriacetic acid | 2.0 g |
| 1-Hydroxyethylidene-1,1-disulfonic acid | 2.0 g |
| Benzyl alcohol | 16 ml |
| Diethylene glycol | 10 ml |
| Sodium sulfite | 2.0 g |
| Potassium bromide | 0.5 g |
| Potassium carbonate | 30 g |
| N-Ethyl-N-(β-methanesulfonamidoethyl)-3-methyl-4-aminoaniline sulfate | 5.5 g |
| Hydroxylamine sulfate | 2.0 g |
| Fluorescent whitening agent (WHITEX 4, manufactured by Sumitomo Chemical Co., Ltd.) | 1.5 g |
| Water to make | 1,000 ml |
| pH at 25° C. | 10.20 |
| Bleach-Fixing Solution | |

-continued

| | |
|---|---|
| Water | 400 ml |
| Ammonium thiosulfate (70% soln.) | 80 ml |
| Ammonium sulfate | 24 g |
| Ammonium iron (III) ethylenediamine-tetraacetate | 30 g |
| Disodium ethylenediaminetetraacetate | 5 g |
| Water to make | 1,000 ml |
| pH at 25° C. | 6.50 |

Rinse Solution

Ion exchanged water (contents of calcium and magnesium each being not more tan 3 ppm).

After processing the color prints thus-obtained, color reproducibility was evaluated. As the result, the color prints obtained from Light-Sensitive Materials 1-1 to 1 6 according to the present invention and comparative Light-Sensitive Material 1-8 were excellent in color reproducibility of blue and green, particularly in comparison with the color print obtained from comparative Light-Sensitive Material 1-7.

Further, in order to evaluate image fastness of the prints, each of the prints was cut in two. One half was stored under ambient conditions and the other half was stored at 60° C. and 70% relative humidity for one month. As a result, with the print obtained from Light-Sensitive Material 1-8 for comparison, color fading was clearly observed although substantially no color fading was recognized with the color prints obtained from Light-Sensitive Materials 1-1 to 1-7.

Therefore, the couplers according to the present invention provide both color reproducibility and image preservability.

EXAMPLE 2

On a paper support, both surfaces of which were laminated with polyethylene, layers were coated as shown below in order to prepare a multilayer color printing paper designated Light-Sensitive Material 2-1. The coating solutions were prepared in the following manner.

Preparation of Coating Solution for First Layer:

19.1 g of Yellow coupler (ExY) and 4.4 g of Color image stabilizer (Cpd-1) were dissolved in a mixture of 27.2 ml of ethyl acetate and 7.7 ml of Solvent (Solv-1). The resulting solution was emulsified and dispersed in 185 ml of a 10% aqueous solution of gelatin containing 8 ml of a 10% aqueous solution of sodium dodecylbenzenesulfonate. Separately, to a silver chlorobromide emulsion (having a bromide content of 1.0 mol% and containing 70 g of silver per kg of the emulsion), $5.0 \times 10^{-4}$ mols of a blue-sensitive sensitizing dye shown below was added per mol of silver to prepare a blue-sensitive emulsion. The above described emulsified dispersion was mixed with the blue-sensitive silver chlorobromide emulsion, with the concentration of the resulting mixture being controlled, to form the composition shown below, i.e., the coating solution for the first layer.

Coating solutions for the second layer to the seventh layer were prepared in a similar manner as described for the coating solution for the first layer.

2-Oxy-4,6-dichloro-s-triazine sodium salt was used as a gelatin hardener in each layer.

The following spectral sensitizing dyes were employed in the emulsion layers as indicated below.

Blue-Sensitive Emulsion Layer:

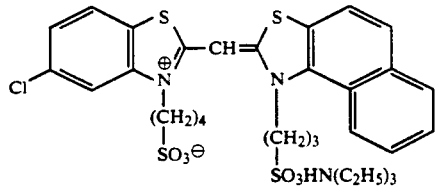

(Amount added: $5.0 \times 10^{-4}$ mol per mol of silver halide)

Green-Sensitive Emulsion Layer:

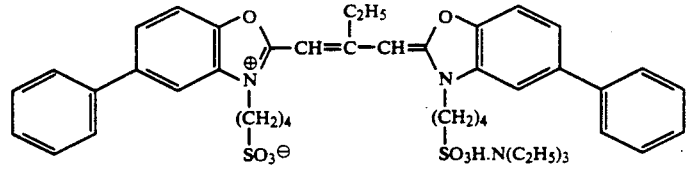

(Amount added: $4.0 \times 10^{-4}$ mol per mol of silver halide)

and

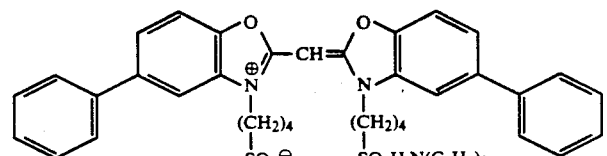

(Amount added: $8.0 \times 10^{-5}$ mol per mol of silver halide)

Red-Sensitive Emulsion Layer:

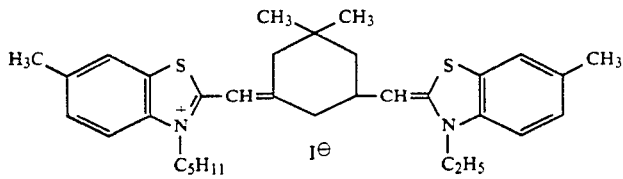

(Amount added: 1.8 × 10⁻⁴ mol per mol of silver halide)

To the red-sensitive emulsion layer, the compound shown below was added in an amount of $2.6 \times 10^{-3}$ mol per mol of silver halide.

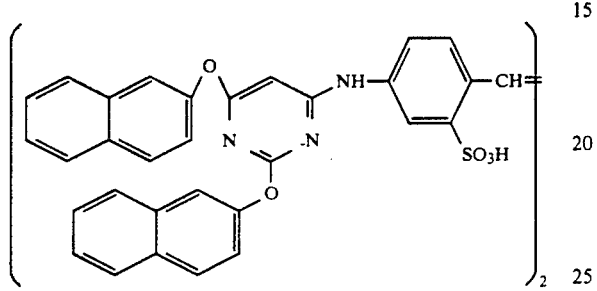

To the blue-sensitive emulsion layer, green-sensitive emulsion layer and red-sensitive emulsion layer, 1-(5-methylureidophenyl)-5-mercaptotetrazole was added in amounts of $8.5 \times 10^{-5}$ mol, $7.7 \times 10^{-4}$ and $2.5 \times 10^{-4}$ mol per mol of silver halide, respectively.

Moreover, in order to prevent irradiation, the following dyes were added to the emulsion layers.

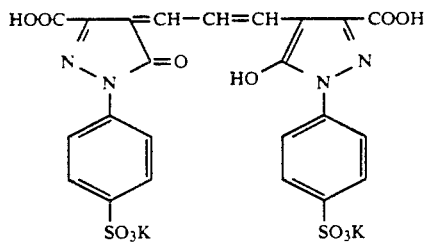

and

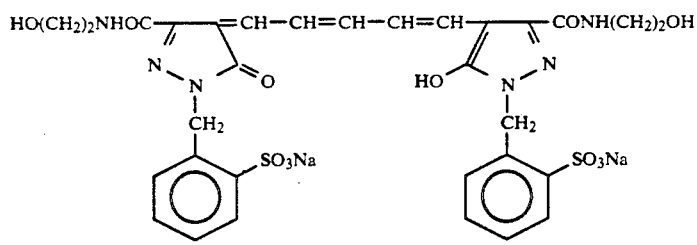

Layer Construction

The composition of each layer is shown below. The numerical values denote the coating amounts of the components in units of g/m². The coating amount of silver halide emulsion is indicated in terms of the silver coating amount.

| | | |
|---|---|---|
| Support | Polyethylene laminated paper (the polyethylene coating containing a white pigment (TiO₂) and a bluish dye | |
| | (ultramarine) on the first layer side) | |
| First Layer (Blue-sensitive layer) | Silver chlorobromide emulsion (Br: 1 mol %) | 0.30 |
| | Gelatin | 1.86 |
| | Yellow coupler (ExY) | 0.82 |
| | Color image stabilizer (Cpd-1) | 0.19 |
| | Solvent (Solv-1) | 0.35 |
| Second Layer (Color mixing preventing layer) | Gelatin | 0.99 |
| | Color mixing preventing agent (Cpd-2) | 0.08 |
| Third Layer (Green-sensitive layer) | Silver chlorobromide emulsion (Br: 1 mol %) | 0.36 |
| | Gelatin | 1.24 |
| | Magenta coupler (ExM) | 0.39 |
| | Color image stabilizer (Cpd-3) | 0.25 |
| | Color image stabilizer (Cpd-4) | 0.12 |
| | Solvent (Solv-2) | 0.25 |
| Fourth Layer (Ultraviolet light absorbing layer) | Gelatin | 1.60 |
| | Ultraviolet light absorbing agent (UV-1) | 0.70 |
| | Color mixing preventing agent (Cpd-5) | 0.05 |
| | Solvent (Solv-3) | 0.42 |
| Fifth Layer (Red-sensitive layer) | Silver chlorobromide emulsion (Br: 1 mol %) | 0.23 |
| | Gelatin | 0.92 |
| | Cyan coupler (ExC) | 0.44 |
| | Color image stabilizer (Cpd-6) | 0.17 |
| | Polymer (Cpd-7) | 0.14 |
| | Solvent (Solv-4) | 0.20 |
| Sixth Layer (Ultraviolet light absorbing layer) | Gelatin | 0.53 |
| | Ultraviolet light absorbing agent (UV-1) | 0.21 |
| | Solvent (Solv-3) | 0.08 |
| Seventh Layer (Protective layer) | Gelatin | 1.33 |
| | Acryl-modified polyvinyl alcohol copolymer (Degree of modification: 17%) | 0.17 |

| -continued | |
|---|---|
| Liquid paraffin | 0.03 |
The compounds used in the above-described layers have the structures shown below respectively.
Yellow coupler (ExY)
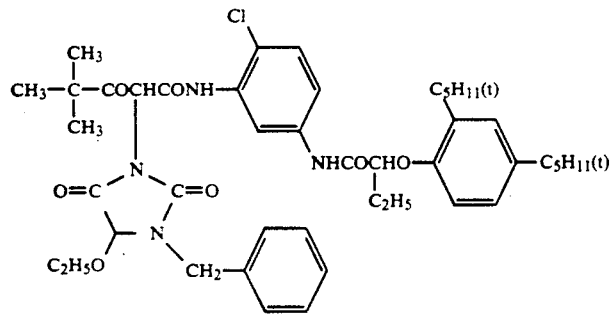
Magenta coupler (ExM)
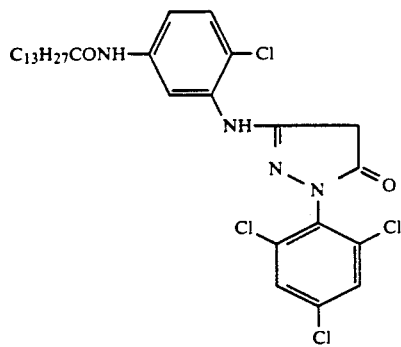
Cyan coupler (ExC) (corresponding to Compound (19))
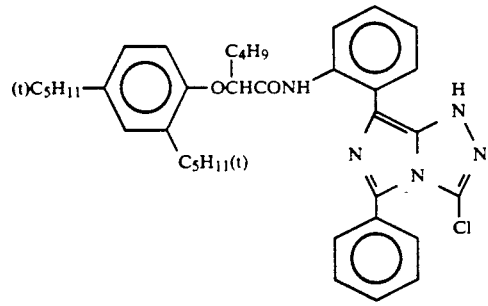
Color image stabilizer (Cpd-1)
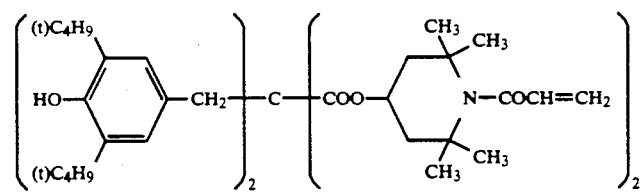
Color mixing preventing agent (Cpd-2)
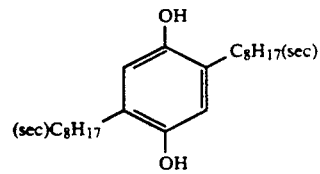

Color image stabilizer (Cpd-3)
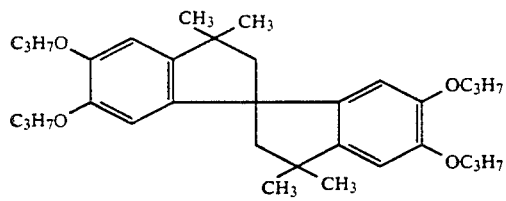
Color image stabilizer (Cpd-4)
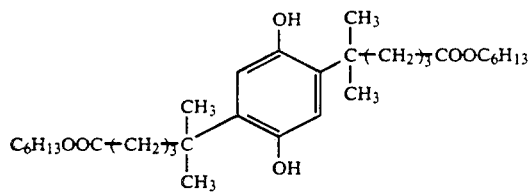
Color mixing preventing agent (Cpd-5)
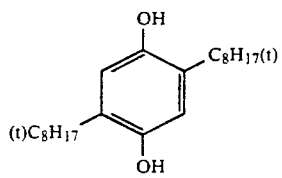
Color image stabilizer (Cpd-6)
A mixture of 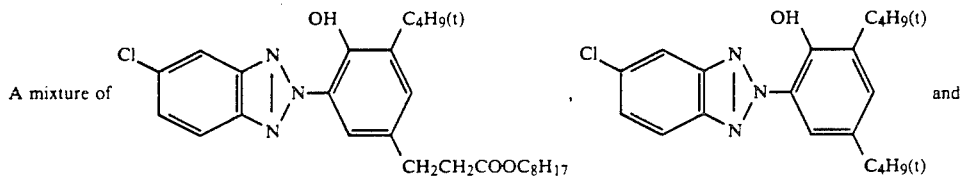
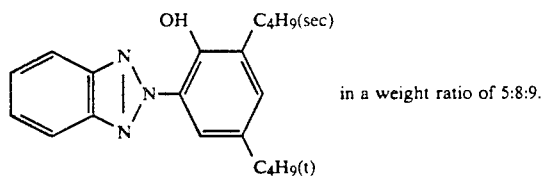 in a weight ratio of 5:8:9.
Polymer (Cpd-7)
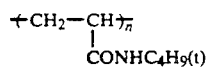
(average molecular weight: 80,000)
Ultraviolet light absorbing agent (UV-1)
A mixture of 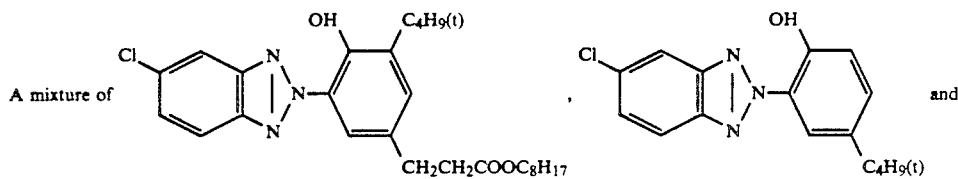
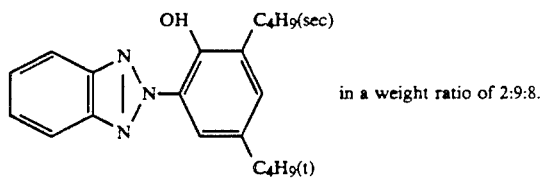 in a weight ratio of 2:9:8.

Solvent (Solv-1)

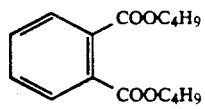

Solvent (Solv-2)

A mixture of $O=P(OCH_2\overset{C_2H_5}{\underset{|}{C}}HC_4H_9)_3$ and 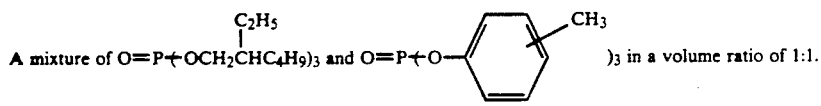 in a volume ratio of 1:1.

Solvent (Solv-3)

$O=P(O-C_9H_{19}\text{-iso})_3$

Solvent (Solv-4)

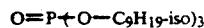

Light-Sensitive Materials 2-2 to 2-8 were prepared in the same manner as described for Light-Sensitive Material 2-1 except for using an equimolar amount of the cyan couplers described in Table 2 below in place of the cyan coupler employed in Light-Sensitive Material 2-1.

TABLE 2

| Light-Sensitive Material | Cyan Coupler | Remark |
|---|---|---|
| 2-1 | 19 | Present Invention |
| 2-2 | 21 | " |
| 2-3 | 24 | " |
| 2-4 | 30 | " |
| 2-5 | 36 | " |
| 2-6 | 41 | " |
| 2-7 | Comparative Compound C | Comparison |
| 2-8 | Comparative Compound B | " |

Comparative Compound C

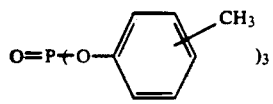

Light-Sensitive Materials 2-1 to 2-8 thus-prepared were printed from a color negative film (Super HR 100 manufactured by Fuji Photo Film Co., Ltd.) having color negative images suitable for evaluating the resulting prints 2-1 to 2-3. The prints were then developed according to the following processing steps.

| Processing Step | Temperature (°C.) | Time |
|---|---|---|
| Color Development | 35 | 45 sec. |
| Bleach-Fixing | 30 to 36 | 45 sec. |
| Stabilizing (1) | 30 to 37 | 20 sec. |
| Stabilizing (2) | 30 to 37 | 20 sec. |
| Stabilizing (3) | 30 to 37 | 20 sec. |
| Stabilizing (4) | 30 to 37 | 30 sec. |
| Drying | 70 to 85 | 60 sec. |

The stabilizing steps were conducted using a four-tank countercurrent system from Stabilizing (4) to Stabilizing (1).

The composition of each processing solution used was as follows:

| Color Developing Solution | |
|---|---|
| Water | 800 ml |
| Ethylenediaminetetraacetic acid | 2.0 g |
| Triethanolamine | 8.0 g |
| Sodium chloride | 1.4 g |
| Potassium carbonate | 25 g |
| N-Ethyl-N-(β-methanesulfonamidoethyl)-3-methyl-4-aminoaniline sulfate | 5.0 g |
| N,N-Diethylhydroxylamine | 4.2 g |
| 5,6-Dihydroxybenzene-1,2,4-trisulfonic acid | 0.3 g |
| Fluorescent brightening agent (4,4-diaminostilbene type) | 2.0 g |
| Water to make | 1000 ml |
| pH (25° C.) | 10.10 |
| Bleach-Fixing Solution | |
| Water | 400 ml |
| Ammonium thiosulfate (70%) | 100 ml |
| Sodium sulfite | 18 g |
| Ammonium ethylenediaminetetraacetate iron (III) | 55 g |
| Disodium ethylenediaminetetraacetate | 3 g |
| Glacial acetic acid | 8 g |
| Water to make | 1,000 ml |
| pH (25° C.) | 5.5 |
| Stabilizing Solution | |
| Formaldehyde (37%) | 0.1 g |
| Formaldehyde-sulfite adduct | 0.7 g |
| 5-Chloro-2-methyl-4-isothiazolin-3-one | 0.02 g |
| 2-Methyl-4-isothiazolin-3-one | 0.01 g |
| Cupric sulfate | 0.005 g |
| Water to make | 1000 ml |
| pH (25° C.) | 4.0 |

Following development processing, color reproducibility and image preservability were evaluated in the same manner as described in Example 1. As a result, the light-sensitive materials of the present invention were found to meet the objectives of the present invention for both color reproducibility and image preservability.

Light-Sensitive materials 2-1 to 2-8 were processed with the same manner, except for changing the processing steps and the components of the processing solution as below. As a result, the coupler of the present invention satisfied both color reproducibility and image preservability.

| Processing Steps | Time | Temperature (C.°) |
|---|---|---|
| Color Development | 45 sec. | 35 |
| Bleach-Fixing | 45 sec. | 35 |
| Water Washing (1) | 30 sec. | 35 |
| Water Washing (2) | 30 sec. | 35 |
| Water Washing (3) | 30 sec. | 35 |
| Drying | 60 sec. | 70 |

The washing steps were conducted using a three tank countercurrent system from Water Washing (3) to Water Washing (1).

The composition of each processing solution used was as follows:

| Color Developing Solution: | |
|---|---|
| Water | 80.0 ml |
| Ethylenediamine -N, N, N', N'-tetramethylene phosphonate | 3.0 g |
| Triethanolamine | 8.0 g |
| Sodium chloride | 1.4 g |
| Potassium carbonate | 25.0 g |
| N-Ethyl-N-(β-methanesulfonamidoethyl)-3-methyl-4-aminoaniline sulfate | 5.0 g |
| N, N-Bis(carboxymethyl)hydrazine | 5.0 g |
| Fluorescent brightening agent (UVITEX CK of Ciba Gaigy AG.) | 1.0 g |
| Water to make | 1,000 ml |
| pH (25° C.) | 10.05 |
| Bleach-Fixing Solution: | |
| Water | 700 ml |
| Ammonium thiosulfate (700 g/l-Solution) | 100 ml |
| Ammonium sulfite | 18 g |
| Ammonium ethylenediaminetetraacetate Fe(III) dihydrate | 55 g |
| Disodium ethylenediaminetetraacetate dihydrate | 3 g |
| Ammonium bromide | 40 g |
| Glacial acetic acid | 8 g |
| Water to make | 1,000 ml |
| pH (25° C.) | 5.5 |

Washing Water:

City water was passed through an ion exchange resin to prepare water containing not more than 3 ppm of calcium and magnesium.

In addition, when the emulsified dispersion of the coupler used in the third layer of Example 1 was used in place of the emulsified dispersion of the coupler used in the third layer of this example, the same result was obtained.

EXAMPLE 3

On a paper support, both surfaces of which were laminated with polyethylene, First Layer to Twelfth Layer were coated as shown below in order to prepare a multilayer color photographic light-sensitive material designated Light-Sensitive Material 3-1. The polyethylene on the First Layer side contained a titanium white pigment and ultramarine as a bluish dye.

Construction of Layers

The components and the coating amounts thereof in terms of g/m² are shown below. The coating amount of silver halide is indicated in terms of the silver coating amount.

| First Layer: Gelatin Layer | |
|---|---|
| Gelatin | 1.30 |
| Second Layer: Antihalation Layer | |
| Black colloidal silver | 0.10 |
| Gelatin | 0.70 |
| Third Layer: Low-Speed Red-Sensitive Layer | |
| Silver iodobromide emulsion (silver iodide: 5.0 mol %; mean grain size: 0.4 μm) spectrally sensitized with Red sensitizing dyes (*1 and *2) | 0.15 |
| Gelatin | 1.00 |
| Cyan coupler (*3) | 0.25 |
| Color fading preventing agent (*5/*6/*7 = 4/4/2 in molar ratio) | 0.10 |
| Coupler solvent (*8 and *9) | 0.06 |
| Fourth Layer: High-Speed Red-Sensitive Layer | |
| Silver iodobromide emulsion (silver iodide: 6.0 mol %; mean grain size: 0.7 μm) spectrally sensitized with Red sensitizing dyes (*1 and *2) | 0.15 |
| Gelatin | 1.00 |
| Cyan coupler (*3) | 0.36 |
| Color fading preventing agent (*5/*6/*7 = 4/4/2 in molar ratio) | 0.15 |
| Coupler solvent (*8/*9 = 1/1 in vol.) | 0.10 |
| Fifth Layer: Intermediate Layer | |
| Magenta colloidal silver | 0.02 |
| Gelatin | 1.00 |
| Color mixing preventing agent (*10) | 0.08 |
| Color mixing preventing agent solvent (*11/*12 = 1/1 in vol.) | 0.16 |
| Polymer latex (*13) | 0.10 |
| Sixth Layer: Low-Speed Green-Sensitive Layer | |
| Silver iodobromide emulsion (silver iodide: 2.5 mol %; mean grain size: 0.4 μm) spectrally sensitized with Green sensitizing dye (*14) | 0.10 |
| Gelatin | 0.80 |
| Magenta coupler (*15) | 0.10 |
| Color fading preventing agent (*16) | 0.10 |
| Stain preventing agent (*17) | 0.01 |
| Stain preventing agent (*18) | 0.001 |
| Coupler solvent (*11/*19 = 1/1 in vol.) | 0.15 |
| Seventh Layer: High-Speed Green-Sensitive Layer | |
| Silver iodobromide emulsion (silver iodide: 3.5 mol %; mean grain size: 0.9 μm) spectrally sensitized with Green sensitizing dye (*14) | 0.10 |
| Gelatin | 0.80 |
| Magenta coupler (*15) | 0.10 |
| Color fading preventing agent (*16) | 0.10 |
| Stain preventing agent (*17) | 0.01 |
| Stain preventing agent (*18) | 0.001 |
| Coupler solvent (*11/*19 = 1/1 in vol.) | 0.15 |
| Eighth Layer: Yellow Filter Layer | |
| Yellow colloidal silver | 0.20 |
| Gelatin | 1.00 |
| Color mixing preventing agent (*10) | 0.06 |
| Color mixing preventing agent solvent (*11/*12 = 1/1 in vol.) | 0.15 |
| Polymer Latex (*13) | 0.10 |
| Ninth Layer: Low-Speed Blue-Sensitive Layer | |
| Silver iodobromide emulsion (silver iodide: 2.5 mol %; mean grain size: 0.5 μm) spectrally sensitized with Blue sensitizing dye (*20) | 0.15 |
| Gelatin | 0.50 |
| Yellow coupler (*21) | 0.20 |
| Stain preventing agent (*18) | 0.001 |
| Coupler solvent (*9) | 0.05 |
| Tenth Layer: High-Speed Blue-Sensitive Layer | |
| Silver iodobromide emulsion (silver iodide: 2.5 mol %; mean grain size: 1.2 μm) spectrally sensitized with Blue sensitizing dye (*20) | 0.25 |
| Gelatin | 1.00 |
| Yellow coupler (*21) | 0.40 |

| -continued | |
|---|---|
| Stain preventing agent (*18) | 0.002 |
| Coupler solvent (*9) | 0.10 |
| Eleventh Layer: Ultraviolet Light Absorbing Layer | |
| Gelatin | 1.50 |
| Ultraviolet light absorbing agent (*22/*6/*7 = 2/4/4 in molar ratio) | 1.00 |
| Color mixing preventing agent (*23) | 0.06 |
| Color mixing preventing agent solvent (*9) | 0.15 |
| Anti-irradiation dye (*24) | 0.02 |
| Anti-irradiation dye (*25) | 0.02 |
| Twelfth Layer: Protective Layer | |
| Fine silver chlorobromide grains (silver chloride: 97 mol %, mean grain size, 0.2 μm) | 0.07 |
| Gelatin | 1.50 |
| Gelatin hardener (*26) | 0.17 |

*1 5,5'-Dichloro-3,3'-di(3-sulfobutyl)-9-ethylthiacarbocyanine sodium salt
*2 Triethylammonium 3-[2-{2-[3-(3-sulfopropyl)naphtho(1,2-d)-thiazolin-2-ylidenemethyl]-1-butenyl}-3-naphtho(1,2-a)-thiazolino]propanesulfonate
*3 Compound 19
*5 2-(2-Hydroxy-3-sec-butyl-5-tert-butylphenyl)benzotriazole
*6 2-(2-Hydroxy-5-tert-butylphenyl)benzotriazole
*7 2-(2-Hydroxy-3,5-di-tert-butylphenyl)-6-chlorobenzotriazole
*8 Di(2-ethylhexyl) phthalate
*9 Trinonyl phosphate
*10 2,5-Di-tert-octylhydroquinone
*11 Tricresyl phosphate
*12 Dibutyl phthalate
*13 Polyethyl acrylate
*14 5,5'-Diphenyl-9-ethyl-3,3'-disulfopropyloxacarboxyamine sodium salt
*15 7-Chloro-6-methyl-2-{1-(2-octyloxy-5-(2-octyloxy-5-tert-octyl)benzenesulfonamido)propyl}-1H-pyrazolo-[1,5-b][1,2,4]triazole
*16 3,3,3',3'-Tetramethyl-5,6,5',6'-tetrapropoxy-1,1'-bisspiroindane
*17 3-(2-Ethylhexyloxycarbonyloxy)-1-(3-hexadecyloxyphenyl)-2-pyrazoline
*18 2-Methyl-5-tert-octylhydroquinone
*19 Trioctyl phosphate
*20 Triethylammonium 3-[2-(3-benzylrhodanin-5-ylidene)-3-benzoxazolynyl]propanesulfonate
*21 α-Pivaloyl-α-[(2,4-dioxo-1-benzyl-5-ethoxyhydantoin-3-yl]-2-chloro-5-(α-2,4-di-tert-amylphenoxy)butanamido]acetanilide
*22 5-Chloro-2-(2-hydroxy-3-tert-butyl-5-tert-octyl)phenyl-benzotriazole
*23 2,5-Di-sec-octylhydroquinone
*24

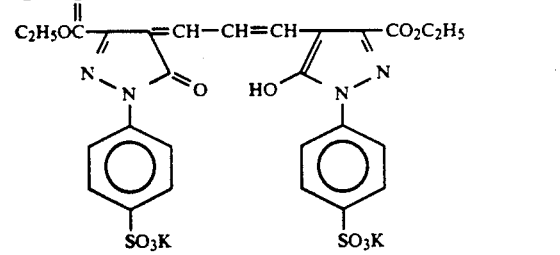

*25

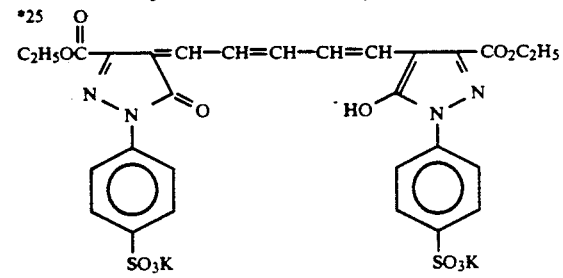

*26 1,2-Bis(vinylsulfonylacetamido)ethane

Light-Sensitive Materials 3-2 to 3-8 were prepared in the same manner as described for Light-Sensitive material 3-1, except for using the equimolar amount of the cyan couplers described in Table 3 below in place of the cyan coupler employed in Light-Sensitive Material 3-1.

TABLE 3

| Light-Sensitive Material | Cyan Coupler | Remark |
|---|---|---|
| 3-1 | 19 | Present Invention |
| 3-2 | 20 | " |
| 3-3 | 22 | " |
| 3-4 | 23 | " |
| 3-5 | 30 | " |
| 3-6 | 36 | " |
| 3-7 | 41 | " |
| 3-8 | Comparative Compound D | Comparison |

Comparative Compound D

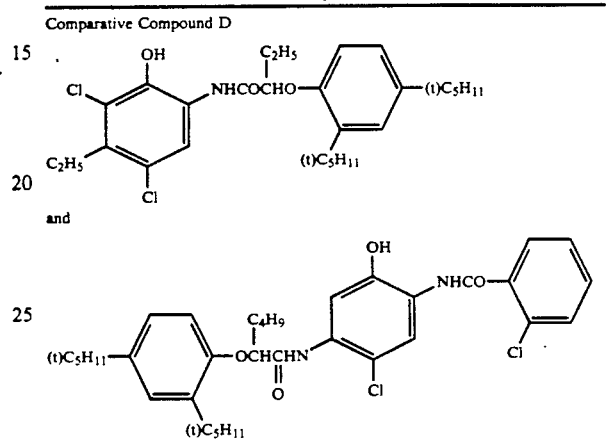

and

A mixture of the above two caplers in a molar ratio of 1:1.

Light-Sensitive Materials 3-1 to 3-8 thus-prepared were printed from a color negative film (Super HR 100 manufactured by Fuji Photo Film Co., Ltd.) having color negative images suitable for evaluating the resulting prints 3-1 to 3-8. The prints were then developed according to the following processing steps.

| Processing Steps | Time | Temperature (°C.) |
|---|---|---|
| First Development (Black- and white development) | 75 sec. | 38 |
| Washing with Water | 90 sec. | 33 |
| Reversal Exposure | 15 sec. | 100 lux (fluorescent lamp) |
| Color Development | 135 sec. | 38 |
| Washing with Water | 45 sec. | 33 |
| Bleach-Fixing | 120 sec. | 38 |
| Washing with Water | 135 sec. | 33 |
| Drying | 45 sec. | 75 |

The processing solutions used had the following compositions.

| First Developing Solution: | |
|---|---|
| Pentasodium nitrilo-N,N,N-trimethylene-phosphonate | 1.0 g |
| Pentasodium diethylenetriamine-pentaacetate | 3.0 g |
| Potassium sulfite | 30.0 g |
| Potassium thiocyanate | 1.2 g |
| Potassium carbonate | 35.0 g |
| Potassium hydroquinonemonosulfonate | 25.0 g |
| 1-Phenyl-4-hydroxymethyl-4-methyl-3-pyrazolidone | 2.0 g |
| Potassium bromide | 0.5 g |
| Potassium iodide | 5.0 mg |
| Water to make | 1,000 ml |

| First Developing Solution: | |
|---|---|
| | pH 9.60 |

The pH was adjusted with hydrochloric acid or potassium hydroxide.

| Color Developing Solution: | |
|---|---|
| Benzyl alcohol | 15.0 ml |
| Diethylene glycol | 12.0 ml |
| 3,6-Dithia-1,8-octanediol | 0.20 g |
| Pentasodium nitrilo-N,N,N-trimethylenephosphonate | 0.5 g |
| Pentasodium diethylenetriaminepentaacetate | 2.0 g |
| Sodium sulfite | 2.0 g |
| Hydroxylamine sulfate | 3.0 g |
| N-Ethyl-N-(β-methanesulfonamidoethyl)-3-methyl-4-aminoaniline sulfate | 5.0 g |
| Fluorescent brightening agent (diaminostilbene type) | 1.0 g |
| Potassium bromide | 0.5 g |
| Potassium iodide | 1.0 mg |
| Water to make | 1,000 ml |
| | pH 10.25 |

The pH was adjusted with hydrochloric acid or potassium hydroxide.

| Bleach-Fixing Solution: | |
|---|---|
| Disodium ethylenediaminetetraacetate dihydrate | 5.0 g |
| Ammonium ethylenediaminetetraacetate Fe(III) monohydrate | 80.0 g |
| Sodium sulfite | 15.0 g |
| Ammonium thiosulfate (700 g/l-Solution) | 160 ml |
| 2-Mercapto-1,3,4-triazole | 0.5 g |
| Water to make | 1,000 ml |
| | pH 6.50 |

The pH was adjusted with acetic acid or aqueous ammonia.

Washing Water:
City water

As a result of the evaluation on color reproducibility of the reversal prints thus-obtained, it was found that the prints obtained from Light-Sensitive Materials 3-1 to 3-7 of the present invention were excellent in color reproducibility of blue and green particularly in comparison with the print obtained from comparative Light-Sensitive Material 3-8 for comparison.

EXAMPLE 4

On a cellulose triacetate film support provided with a subbing layer, each layer having the composition set forth below was coated to prepare a multilayer color light-sensitive material designated light-sensitive material 401.

With respect to the compositions of the layers, the coating amounts of silver halide and colloidal silver are shown in units of g/m² of silver, the coating amounts of the couplers, additives and gelatin are shown in units of g/m², and the coating amounts of the sensitizing dyes are shown by mol per mol of the silver halide present in the same layer.

| First Layer: Antihalation Layer | |
|---|---|
| Black colloidal silver | 0.2 |
| Gelatin | 1.3 |
| ExM-9 | 0.06 |
| UV-1 | 0.03 |
| UV-2 | 0.06 |
| UV-3 | 0.06 |
| Solv-1 | 0.15 |
| Solv-2 | 0.15 |
| Solv-3 | 0.05 |
| Second Layer: Intermediate Layer | |
| Gelatin | 1.0 |
| UV-1 | 0.03 |
| ExC-4 | 0.02 |
| ExF-1 | 0.004 |
| Solv-1 | 0.1 |
| Solv-2 | 0.1 |
| Third Layer: Low-Speed Red-Sensitive Emulsion Layer | |
| Silver iodobromide emulsion (AgI: 4 mol %, uniform AgI type, diameter corresponding to sphere: 0.5 μm, coefficient of variation of diameter corresponding to sphere: 20%, tabular grain, diameter/thickness ratio: 3.0) | 1.2 g (as silver) |
| Silver iodobromide emulsion (AgI: 3 mol %, uniform AgI type, diameter corresponding to sphere: 0.3 μm, coefficient of variation of diameter corresponding to sphere: 15%, spherical grain, diameter/thickness ratio: 1.0) | 0.6 g (as silver) |
| Gelatin | 1.0 |
| ExS-1 | $4 \times 10^{-4}$ |
| ExS-2 | $5 \times 10^{-5}$ |
| ExC-1 | 0.66 |
| ExC-3 | 0.03 |
| ExC-4 | 0.12 |
| ExC-5 | 0.01 |
| Fourth Layer: High-Speed Red-sensitive Emulsion Layer | |
| Silver iodobromide emulsion (AgI: 6 mol %, internal high AgI type, with core/shell ratio of 1:1, diameter corresponding to sphere: 0.7 μm, coefficient of variation of diameter corresponding to sphere: 15%, tabular grain, diameter/thickness ratio: 5.0) | 0.7 g (as silver) |
| Gelatin | 1.0 |
| ExS-1 | $3 \times 10^{-4}$ |
| ExS-2 | $2.3 \times 10^{-5}$ |
| ExC-1 | 0.09 |
| ExC-7 | 0.05 |
| ExC-4 | 0.05 |
| Solv-1 | 0.05 |
| Solv-3 | 0.05 |
| Fifth Layer: Intermediate Layer | |
| Gelatin | 0.5 |
| Cpd-1 | 0.1 |
| Solv-1 | 0.05 |
| Sixth Layer: Low-Speed Green-Sensitive Emulsion Layer | |
| Silver iodobromide emulsion (AgI: 4 mol %, surface high AgI type, with core/shell ratio of 1:1, diameter corresponding to sphere: 0.5 μm, coefficient of variation of diameter corresponding to sphere: 15%, tabular grain, diameter/thickness ratio: 4.0) | 0.35 g (as silver) |
| Silver iodobromide emulsion (AgI: 3 mol %, uniform AgI type, diameter corresponding to sphere: 0.3 μm, coefficient of variation of diameter corresponding to sphere: 25%, spherical grain, diameter/thickness ratio: 1.0) | 0.20 (as silver) |
| Gelatin | 1.0 |
| ExS-3 | $5 \times 10^{-4}$ |
| ExS-4 | $3 \times 10^{-4}$ |
| ExS-5 | $1 \times 10^{-4}$ |

| | |
|---|---|
| ExM-8 | 0.4 |
| ExM-9 | 0.07 |
| ExM-10 | 0.02 |
| ExY-11 | 0.03 |
| Solv-1 | 0.3 |
| Solv-4 | 0.05 |

Seventh Layer: High-Speed Green-Sensitive Emulsion Layer

| | |
|---|---|
| Silver iodobromide emulsion (AgI: 4 mol %, internal high AgI type, with core/shell ratio of 1:3, diameter corresponding to sphere: 0.7 μm, coefficient of variation of diameter corresponding to sphere: 20%, tabular grain, diameter/thickness ratio: 5.0) | 0.8 (as silver) |
| Gelatin | 0.5 |
| ExS-3 | $5 \times 10^{-4}$ |
| ExS-4 | $3 \times 10^{-4}$ |
| ExS-5 | $1 \times 10^{-4}$ |
| ExM-8 | 0.1 |
| ExM-9 | 0.02 |
| ExY-11 | 0.03 |
| ExC-2 | 0.03 |
| ExM-14 | 0.01 |
| Solv-1 | 0.2 |
| Solv-4 | 0.01 |

Eighth Layer: Intermediate Layer

| | |
|---|---|
| Gelatin | 0.5 |
| Cpd-1 | 0.05 |
| Solv-1 | 0.02 |

Ninth Layer: Donor Layer of Interimage Effect to Red-Sensitive Layer

| | |
|---|---|
| Silver iodobromide emulsion (AgI: 2 mol %, internal high AgI type, with core/shell ratio of 2:1, diameter corresponding to sphere: 1.0 μm, coefficient of variation of diameter corresponding to sphere: 15%, tabular grain, diameter/thickness ratio: 6.0) | 0.35 (as silver) |
| Silver iodobromide emulsion (AgI: 2 mol %, internal high AgI type, diameter corresponding to sphere: 0.4 μm, coefficient of variation of diameter corresponding to sphere: 20%, tabular grain, diameter/thickness ratio: 6.0) | 0.20 (as silver) |
| Gelatin | 0.5 |
| ExS-3 | $8 \times 10^{-4}$ |
| ExY-13 | 0.11 |
| ExM-12 | 0.03 |
| ExM-14 | 0.10 |
| Solv-1 | 0.20 |

Tenth Layer: Yellow Filter Layer

| | |
|---|---|
| Yellow Colloidal Silver | 0.05 |
| Gelatin | 0.5 |
| Cpd-2 | 0.13 |
| Solv-1 | 0.13 |
| Cpd-1 | 0.10 |

Eleventh Layer: Low-Speed Blue-sensitive Emulsion Layer

| | |
|---|---|
| Silver iodobromide emulsion (AgI: 4.5 mol %, uniform AgI type, diameter corresponding to sphere: 0.7 μm, coefficient of variation of diameter corresponding to sphere: 15%, tabular grain, diameter/thickness ratio: 7.0) | 0.3 (as silver) |
| Silver iodobromide emulsion (AgI: 3 mol %, uniform AgI type, diameter corresponding to sphere: 0.3 μm, coefficient of variation of diameter corresponding to sphere: 25%, tabular grain, diameter/thickness ratio: 7.0) | 0.15 (as silver) |
| Gelatin | 1.6 |
| ExS-6 | $2 \times 10^{-4}$ |
| ExC-16 | 0.05 |
| ExC-2 | 0.10 |
| ExC-3 | 0.02 |
| ExY-13 | 0.07 |
| ExY-15 | 1.0 |
| Solv-1 | 0.20 |

Twelfth Layer: High-Speed Blue-sensitive Emulsion Layer

| | |
|---|---|
| Silver iodobromide emulsion (AgI: 10 mol %, internal high AgI type, diameter corresponding to sphere: 1.0 μm, coefficient of variation of diameter corresponding to sphere: 25%, multiple twin tabular grain, diameter/thickness ratio: 2.0) | 0.5 (as silver) |
| Gelatin | 0.5 |
| ExS-6 | $1 \times 10^{-4}$ |
| ExY-15 | 0.20 |
| ExY-13 | 0.01 |
| Solv-1 | 0.10 |

Thirteenth Layer: First Protective Layer

| | |
|---|---|
| Gelatin | 0.8 |
| UV-4 | 0.1 |
| UV-5 | 0.15 |
| Solv-1 | 0.01 |
| Solv-2 | 0.01 |

Fourteenth Layer: Second Protective Layer

| | |
|---|---|
| Fine grain silver iodobromide emulsion (AgI: 2 mol %, uniform AgI type, diameter corresponding to sphere: 0.07 μm) | 0.5 (as silver) |
| Gelatin | 0.45 |
| Polymethyl methacrylate particle (diameter: 1.5 μm) | 0.2 |
| H-1 | 0.4 |
| Cpd-5 | 0.5 |
| Cpd-6 | 0.5 |

Each layer described above further contained a emulsion stabilizer (Cpd-3: 0.04 g/m²) and a surface active agent (Cpd-4: 0.02 g/m²) as a coating aid in addition to the above-described compounds.

The compounds used for the preparation of the light-sensitive material are illustrated below.

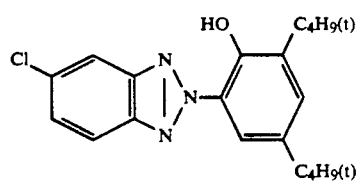

UV-1

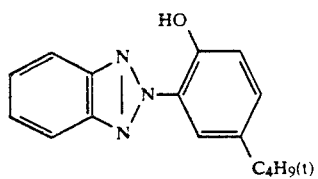 UV-2
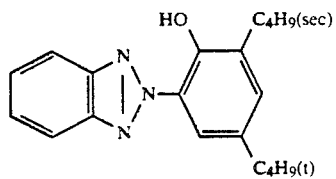 UV-3
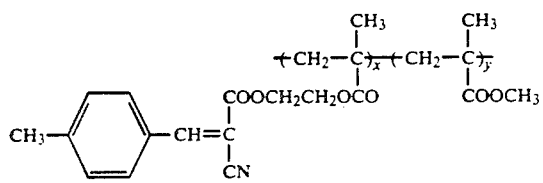 UV-4
(x/y = 7/3 by weight)
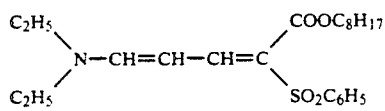 UV-5
Tricresyl phosphate — Solv-1
Dibutyl phthalate — Solv-2
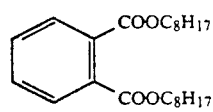 Solv-3
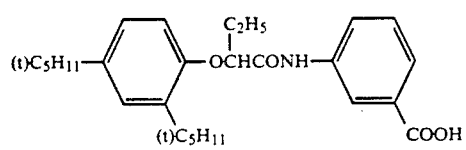 Solv-4
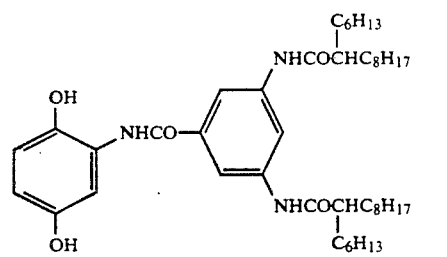 Cpd-1
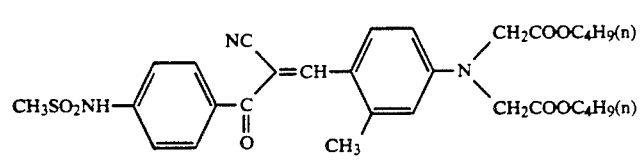 Cpd-2
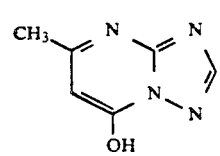 Cpd-3

-continued
Cpd-4
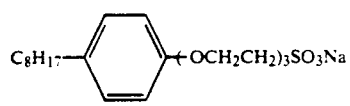
Cpd-5
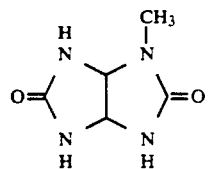
Cpd-6
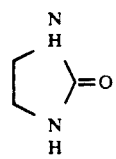
(corresponding to Compound (19))
ExC-1
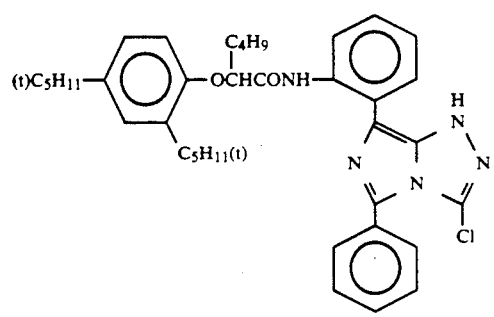
ExC-2
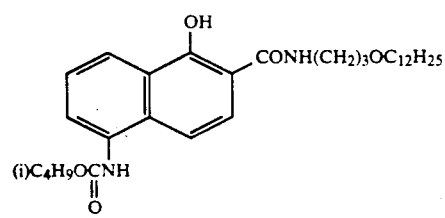
ExC-3
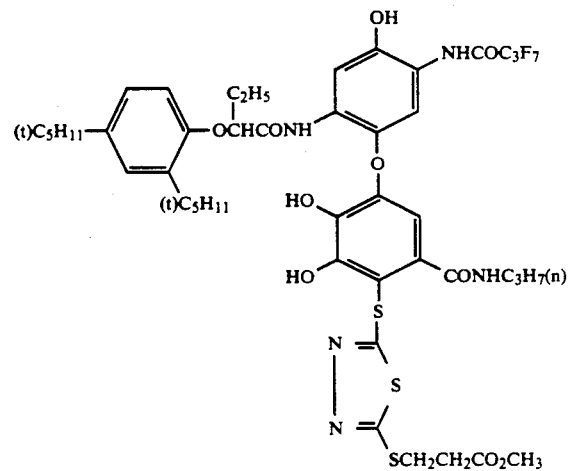

-continued
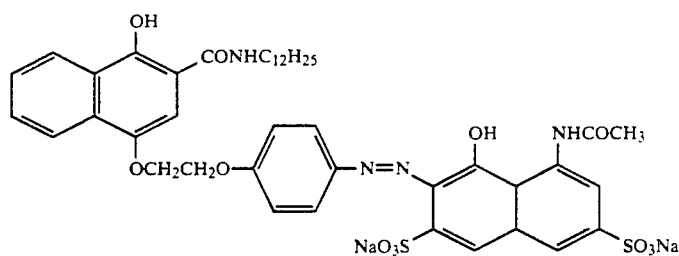
ExC-4
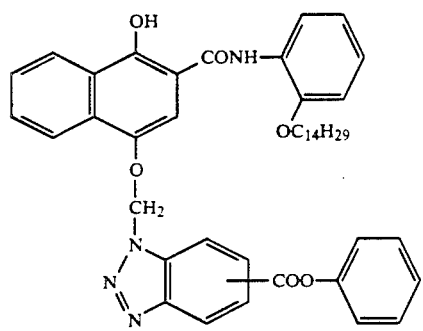
ExC-5
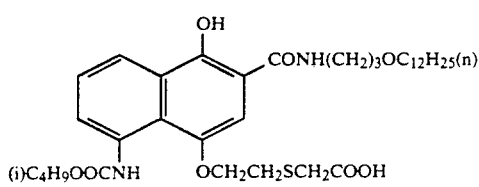
ExC-7
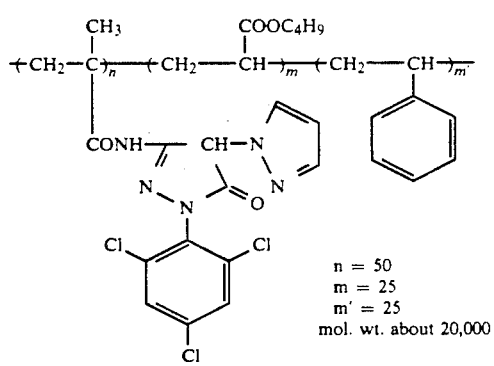
ExM-8
n = 50
m = 25
m' = 25
mol. wt. about 20,000
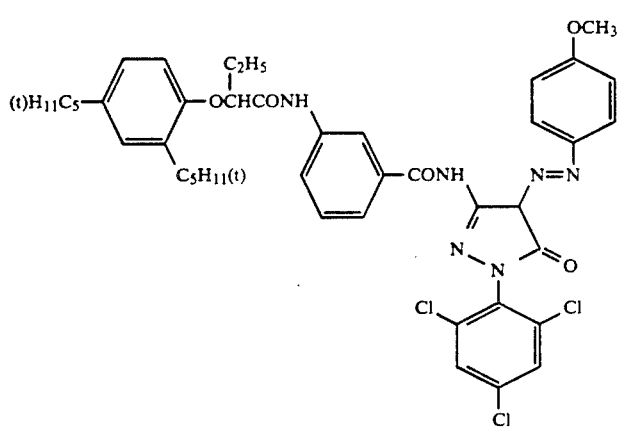
ExM-9

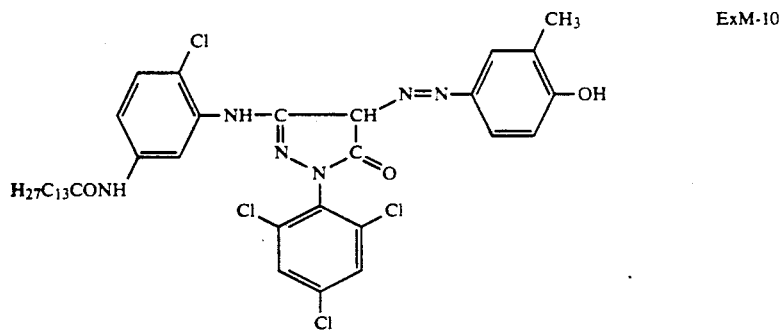
ExM-10
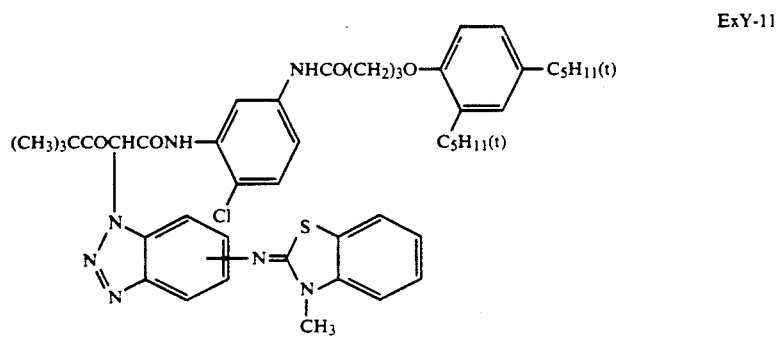
ExY-11
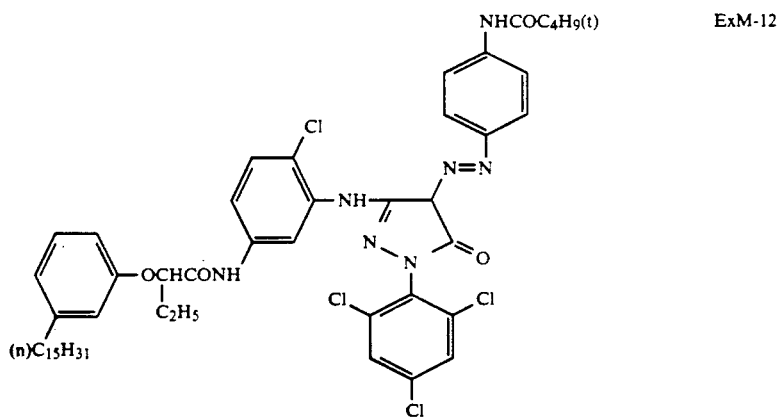
ExM-12
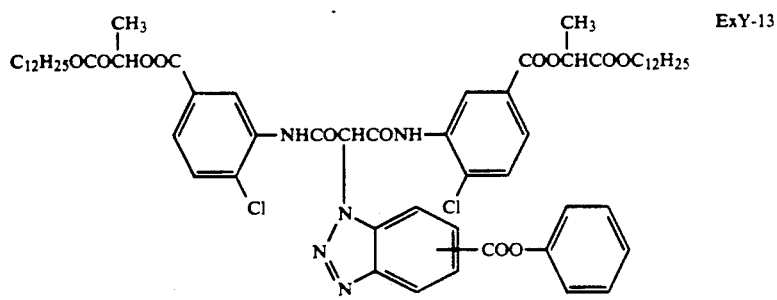
ExY-13

-continued
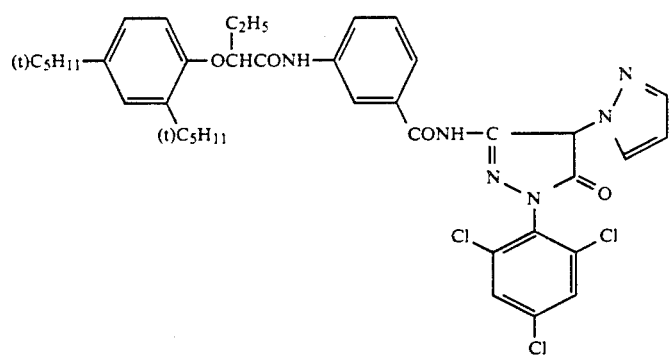
ExM-14
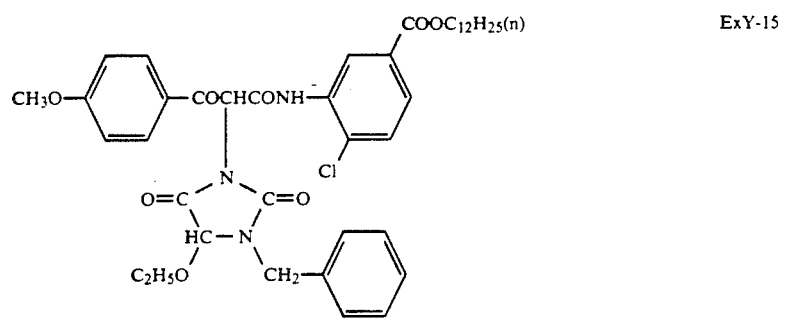
ExY-15
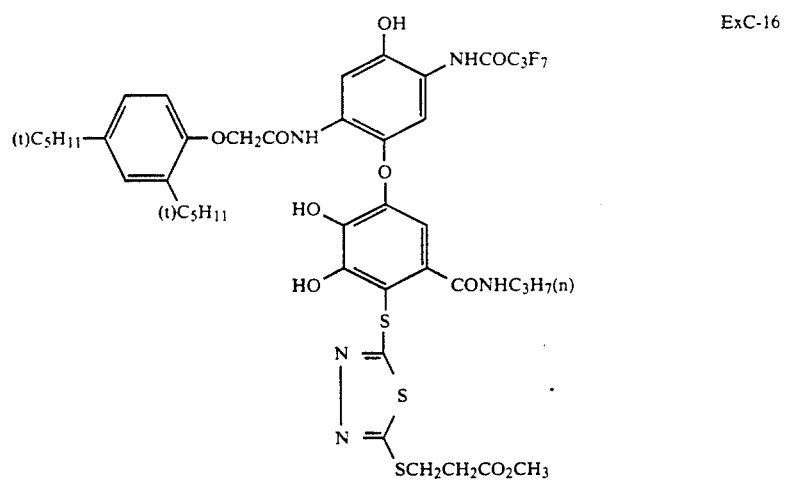
ExC-16
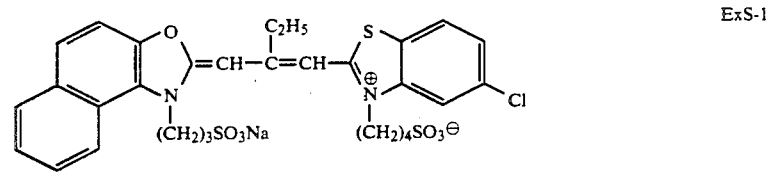
ExS-1
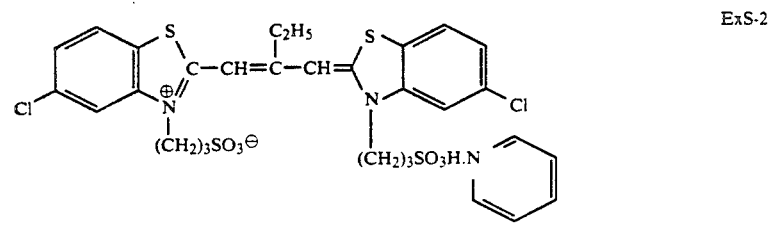
ExS-2

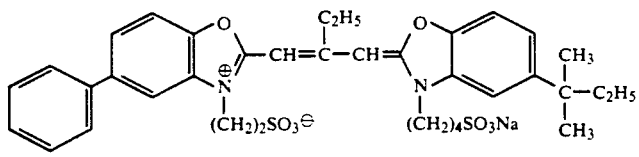

ExS-3

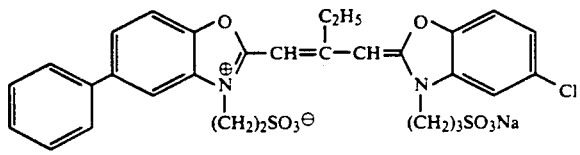

ExS-4

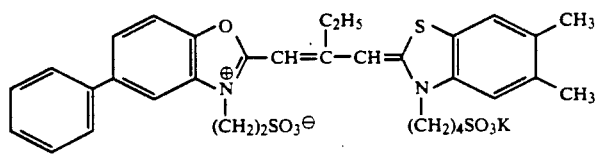

ExS-5

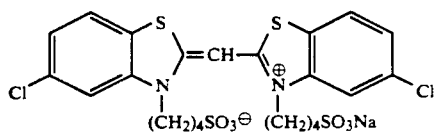

ExS-6

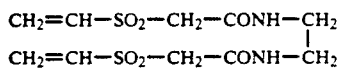

H-1

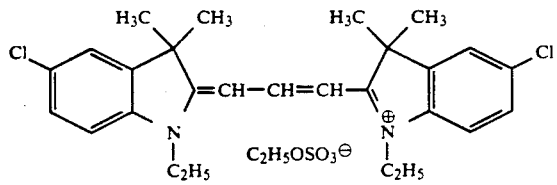

ExF-1

Light-Sensitive Materials 402 to 407 were prepared in the same manner as described for Light-Sensitive Material 401 except for using an equimolar amount of the cyan couplers described in Table 4 below in place of cyan coupler ExC-1 (corresponding to Compound (19)) of the present invention employed in the third layer and fourth layer of Light-Sensitive Material 401.

TABLE 4

| Light-Sensitive Material | Cyan Coupler Used in Third Layer and Fourth Layer | Remark |
|---|---|---|
| 401 | 19 | Present Invention |
| 402 | 21 | " |
| 403 | 24 | " |
| 404 | 30 | " |
| 405 | 36 | " |
| 406 | 41 | " |
| 407 | Comparative Compound E | Comparison |

Comparative Compound E (corresponding to ExC-2)

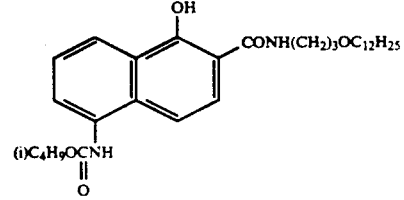

Light-Sensitive Materials 401 to 407 thus prepared were cut into a 35 m/m width strip and used to photo-graph typical subjects. The exposed color negative materials were then developed according to the following processing steps.

| Processing Step | Processing Time | Processing Temperature (°C.) |
|---|---|---|
| Color Development | 3 min. 15 sec. | 38 |
| Bleaching | 1 min. 00 sec. | 38 |
| Bleach-Fixing | 3 min. 15 sec. | 38 |
| Washing with Water (1) | 40 sec. | 35 |
| Washing with Water (2) | 1 min. 00 sec. | 35 |
| Stabilizing | 40 sec. | 38 |
| Drying | 1 min. 15 sec. | 55 |

The composition of each processing solution used is illustrated below.

| Color Developing Solution: | |
|---|---|
| Diethylenetriaminepentaacetic acid | 1.0 g |
| 1-Hydroxyethylidene-1,1-diphosphonic acid | 3.0 g |
| Sodium sulfite | 4.0 g |
| Potassium carbonate | 30.0 g |
| Potassium bromide | 1.4 g |
| Potassium iodide | 1.5 mg |
| Hydroxylamine sulfate | 2.4 g |
| 4-(N-Ethyl-N-β-hydroxyethylamino)-2-methyleniline sulfate | 4.5 g |

-continued

| Water to make | 1.0 l |
|---|---|
| pH | 10.05 |
| Bleaching Solution: | |
| Ammonium iron (III) ethylenediamine-tetraacetate dihydrate | 120.0 g |
| Disodium ethylenediaminetetraacetate | 10.0 g |
| Ammonium bromide | 100.0 g |
| Ammonium nitrate | 10.0 g |
| Bleach accelerating agent | 0.005 ml |

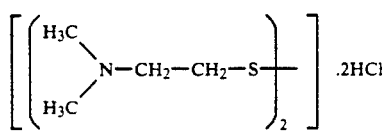

| Aqueous ammonia (27%) | 15.0 ml |
|---|---|
| Water to make | 1.0 l |
| pH | 6.3 |
| Bleach-Fixing Solution: | |
| Ammonium iron (III) ethylenediamine-tetraacetate dihydrate | 50.0 g |
| Disodium ethylenediaminetetraacetate | 5.0 g |
| Sodium sulfite | 12.0 g |
| Aqueous solution of ammonium thiosulfate (70%) | 240.0 ml |
| Aqueous ammonia (27%) | 6.0 ml |
| Water to make | 1.0 l |
| pH | 7.2 |

Washing Water:

City water was passed through a mixed bed type column filled with an H type strong acidic cation exchange resin (Amberlite IR-120B manufactured by Rhom & Hass Co.) and an OH type anion exchange resin (Amberlite IRA-400 manufactured by Rhom & Hass Co.) to prepare water containing not more than 3 mg/l of calcium ion and magnesium ion. Sodium dichloroisocyanulate was added to the water thus treated in an amount of 20 mg/l and sodium sulfate in an amount of 0.15 g/l. The pH of the washing water was in the range of from 6.5 to 7.5.

| Stabilizing Solution: | |
|---|---|
| Formalin (37%) | 2.0 ml |
| Polyoxyethylene-p-monononylphenylether (average degree of polymerization: 10) | 0.3 g |
| Disodium ethylenediaminetetraacetate | 0.05 g |
| Water to make | 1.0 l |
| pH | 5.0 to 8.0 |

Color prints were then made from each of the developed color negative films using a color printer, and the color paper were subjected to standard development processing to prepare color prints. As a result, it was found that the color prints obtained from the negative films of Light-Sensitive Materials 401 to 406 of the present invention were excellent in color reproducibility as compared with the color print obtained from the negative film of comparative Light-Sensitive Material 407.

EXAMPLE 5

On a cellulose triacetate film support, were coated the first layer to the fourteenth layer shown below was coated in order to prepare a multilayer color photographic light-sensitive material designated Light-Sensitive Material 501.

Compositions of Light-Sensitive Layers:

The components used in each layer and the coating amounts thereof are in units of g/m². The coating amount of silver halide is indicated in terms of the silver coating amount.

| First Layer: Antihalation Layer | |
|---|---|
| Black colloidal silver | 0.30 |
| Gelatin | 2.50 |
| UV-1 | 0.05 |
| UV-2 | 0.10 |
| UV-3 | 0.10 |
| Solv-1 | 0.10 |
| Second Layer: Intermediate Layer | |
| Gelatin | 0.50 |
| Third Layer: Low-Speed Red-Sensitive Layer | |
| Monodispersed silver iodobromide emulsion (silver iodide: 4 mol %, cubic, average particle size: 0.3 μm, coefficient of variation: 15%) | 0.50 |
| ExS-1 | $1.40 \times 10^{-3}$ |
| ExS-2 | $6.00 \times 10^{-5}$ |
| Gelatin | 0.80 |
| ExC-1 | 0.30 |
| Solv-2 | 0.10 |
| Fourth Layer: Medium-Speed Red-Sensitive Layer | |
| Monodispersed silver iodobromide emulsion (silver iodide: 2.5 mol %, tetradecahedral, average particle size: 0.45 μm, coefficient of variation: 15%) | 0.50 |
| ExS-1 | $1.60 \times 10^{-3}$ |
| ExS-2 | $6.00 \times 10^{-5}$ |
| Gelatin | 1.00 |
| ExC-1 | 0.45 |
| Solv-2 | 0.20 |
| Fifth Layer: High-Speed Red-Sensitive Layer | |
| Monodispersed silver iodobromide emulsion (silver iodide: 2.5 mol %, tetradecahedral, average particle size: 0.60 μm, coefficient of variation: 15%) | 0.30 |
| ExS-1 | $1.60 \times 10^{-3}$ |
| ExS-2 | $6.00 \times 10^{-5}$ |
| Gelatin | 0.70 |
| ExC-1 | 0.30 |
| Solv-2 | 0.12 |
| Sixth Layer: Intermediate Layer | |
| Gelatin | 1.00 |
| Cpd-1 | 0.1 |
| Solv-1 | 0.03 |
| Solv-2 | 0.08 |
| Solv-3 | 0.12 |
| Cpd-2 | 0.25 |
| Seventh Layer: Low-Speed Green-Sensitive Layer | |
| Silver iodobromide emulsion (silver iodide: 3.0 mol %, mixture of regular crystals and twin crystals, average particle size: 0.3 μm) | 0.65 |
| ExS-3 | $3.30 \times 10^{-3}$ |
| ExS-4 | $1.50 \times 10^{-3}$ |
| Gelatin | 1.50 |
| ExM-1 | 0.10 |
| ExM-2 | 0.25 |
| Solv-2 | 0.30 |
| Eighth Layer: High-Speed Green-Sensitive Layer | |
| Tabular silver iodobromide emulsion (silver iodide: 2.5 mol %, particles having a diameter/thickness ratio of 5 or more occupying 50% of the projected area of the total particles, average thickness: 0.15 μm) | 0.70 |
| ExS-3 | $1.30 \times 10^{-3}$ |
| ExS-4 | $5.00 \times 10^{-4}$ |
| Gelatin | 1.00 |
| ExM-3 | 0.25 |
| Cpd-3 | 0.10 |
| Cpd-4 | 0.05 |
| Solv-2 | 0.05 |
| Ninth Layer: Intermediate Layer | |
| Gelatin | 0.50 |
| Tenth Layer: Yellow Filter Layer | |
| Yellow colloidal silver | 0.10 |

| | |
|---|---|
| Gelatin | 1.00 |
| Cpd-1 | 0.05 |
| Solv-1 | 0.03 |
| Solv-2 | 0.07 |
| Cpd-2 | 0.10 |
| Eleventh Layer: Low-Speed Blue-Sensitive Layer | |
| Silver iodobromide emulsion (silver iodide: 2.5 mol %, mixture of regular crystals and twin crystals, average particle size: 0.7 μm) | 0.55 |
| ExS-5 | $1.00 \times 10^{-3}$ |
| Gelatin | 0.90 |
| ExY-1 | 0.50 |
| Solv-2 | 0.10 |
| Twelfth Layer: High-Speed Blue-Sensitive Layer | |
| Tabular silver iodobromide emulsion (silver iodide: 2.5 mol %, particles having a diameter/thickness ratio of 5 or more occupying 50% of the projected area of the total particles, average thickness: 0.13 μm) | 1.00 |
| ExS-5 | $1.70 \times 10^{-3}$ |
| Gelatin | 2.00 |
| ExY-1 | 1.00 |
| Solv-2 | 0.20 |
| Thirteenth Layer: | |
| Ultraviolet Light Absorbing Layer | |
| Gelatin | 1.50 |
| UV-1 | 0.02 |
| UV-2 | 0.04 |
| UV-3 | 0.04 |
| Cpd-5 | 0.30 |
| Solv-1 | 0.30 |
| Cpd-6 | 0.10 |
| Fourteenth Layer: Protective Layer | |
| Fine grain silver iodobromide (silver iodide: 1 mol %, average particle size: 0.05 μm) | 0.10 |
| Gelatin | 2.00 |
| H-1 | 0.30 |

The compounds used in the above-described layers are illustrated below.

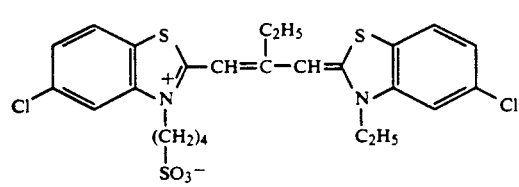
ExS-1

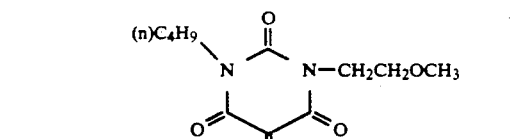
ExS-2

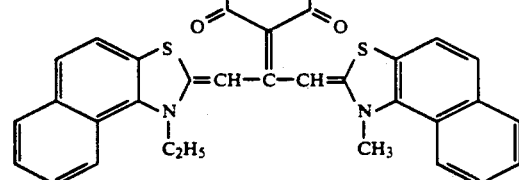
ExS-3

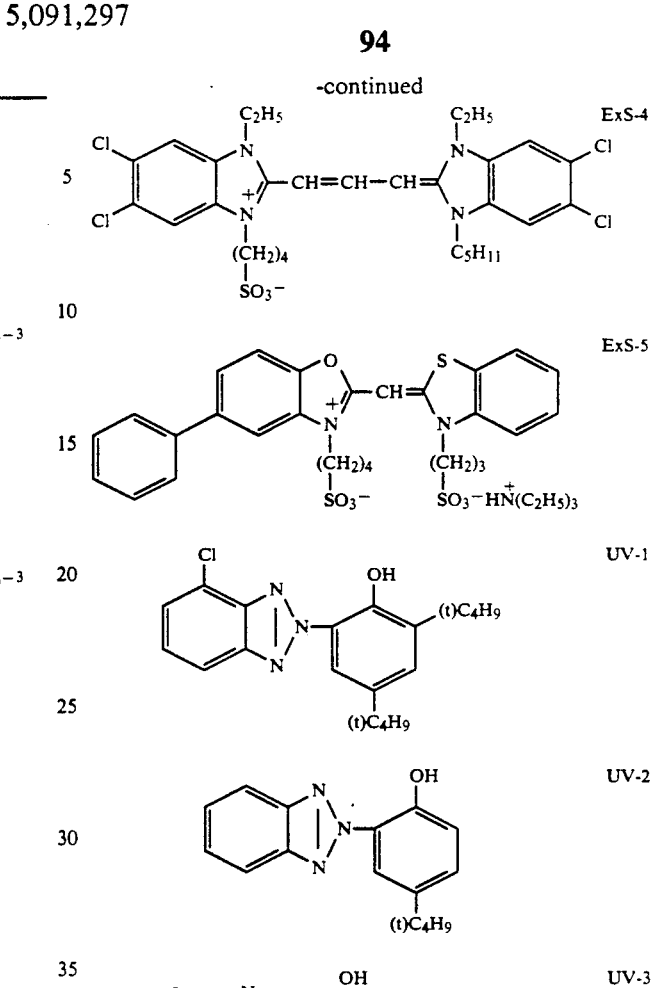

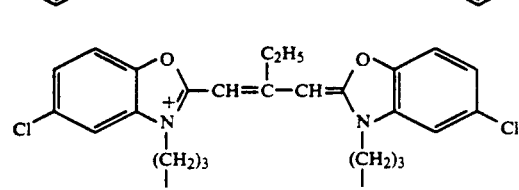
Cpd-4

-continued

Cpd-5
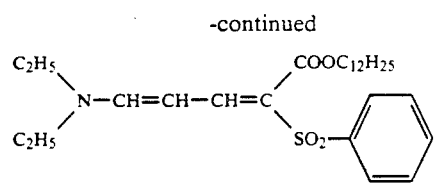

Cpd-6
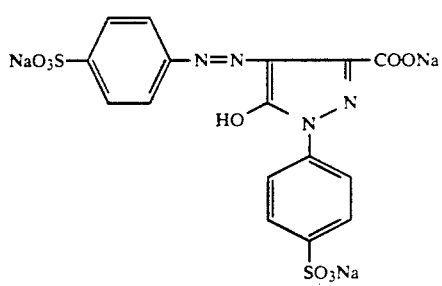
(corresponding to Compound (19))

ExC-1
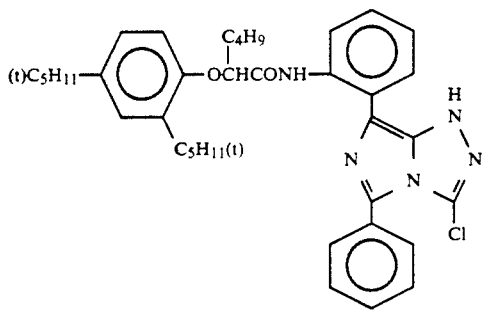

ExM-1
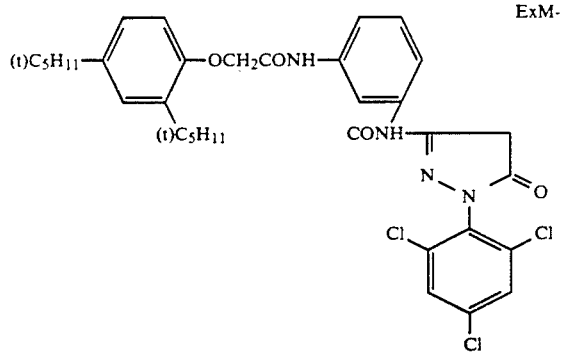

ExM-2
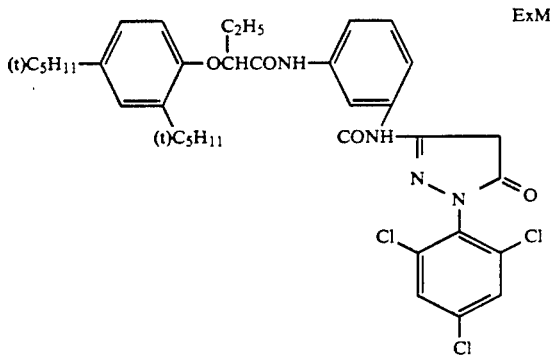

ExM-3
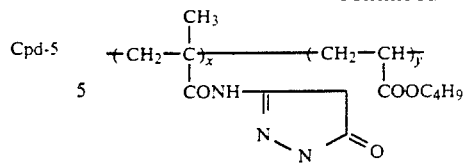
(x/y = 50/50 by wt. %)

ExY-1
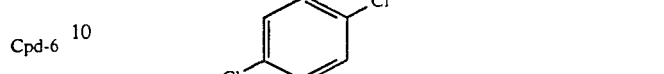

Solv-1: Dibutyl phthalate
Solv-2: Tricresyl phosphate
Solv-3: Trinonyl phosphate
H-1: 1,2-Bis(vinylsulfonylacetamido)ethane Light-Sensitive Materials 502 to 509 were prepared in the same manner as described for Light-Sensitive Material 501 except for using an equimolar amount of the cyan couplers as shown in Table 5 below in place of the cyan coupler (ExC-1) employed in the third layer, fourth layer and fifth layer of Light-Sensitive Material 501.

TABLE 5

| Light-Sensitive Material | Cyan Coupler | Remark |
|---|---|---|
| 501 | 19 | Present Invention |
| 502 | 20 | " |
| 503 | 21 | " |
| 504 | 23 | " |
| 505 | 24 | " |
| 506 | 30 | " |
| 507 | 36 | " |
| 508 | 41 | " |
| 509 | Comparative Compound F | Comparison |

Comparative Compound F
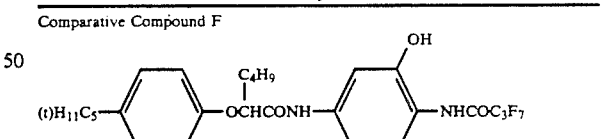

Light-Sensitive Materials 501 to 509 thus prepared were cut into 35 m/m width strip, and used to photograph typical subjects. The exposed light-sensitive materials were then developed according to the following processing steps.

| Processing Step | Time | Temperature (°C.) |
|---|---|---|
| First Development | 6 minutes | 38 |
| Washing with Water | 2 minutes | 38 |
| Reversal | 2 minutes | 38 |
| Color Development | 6 minutes | 38 |

-continued

| Processing Step | Time | Temperature (°C.) |
|---|---|---|
| Controlling | 2 minutes | 38 |
| Bleaching | 6 minutes | 38 |
| Fixing | 4 minutes | 38 |
| Washing with Water | 4 minutes | 38 |
| Stabilizing | 1 minute | 25 |

The composition of each processing solution used was as follows:

| First Developing Solution: | |
|---|---|
| Pentasodium nitrilo-N,N,N-trimethylene-phosphate | 2.0 g |
| Sodium sulfite | 30 g |
| Potassium hydroquinonemonosulfonate | 20 g |
| Potassium carbonate | 33 g |
| 1-Phenyl-4-methyl-4-hydroxymethyl-3-pyrazolidone | 2.0 g |
| Potassium bromide | 2.5 g |
| Potassium thiocyanate | 1.2 g |
| Potassium iodide | 2.0 mg |
| Water to make | 1000 ml |
| pH | 9.60 |

The pH was adjusted with hydrochloric acid or potassium hydroxide.

| Reversal Solution: | |
|---|---|
| Pentasodium nitrilo-N,N,N-trimethylene-phosphate | 3.0 g |
| Stannous chloride dihydrate | 1.0 g |
| p-Aminophenol | 0.1 g |
| Sodium hydroxide | 8 g |
| Glacial acetic acid | 15 ml |
| Water to make | 1000 ml |
| pH | 6.00 |

The pH was adjusted with hydrochloric acid or sodium hydroxide.

| Color Developing Solution: | |
|---|---|
| Pentasodium nitrilo-N,N,N-trimethylene-phosphonate | 2.0 g |
| Sodium sulfite | 7.0 g |
| Sodium tertiary phosphate 12 hydrate | 36 g |
| Potassium bromide | 1.0 g |
| Potassium iodide | 90 mg |
| Sodium hydroxide | 3.0 g |
| Citrazinic acid | 1.5 g |
| N-Ethyl-N-(β-methanesulfonamidoethyl)-3-methyl-4-aminoaniline sulfate | 11 g |
| 3,6-Dithiaoctane-1,8-diol | 1.0 g |
| Water to make | 1000 ml |
| pH | 11.80 |

The pH was adjusted with hydrochloric acid or potassium hydroxide.

| Controlling Solution: | |
|---|---|
| Disodium ethylenediaminetetraacetate dihydrate | 8.0 g |
| Sodium sulfite | 12 g |
| 1-Thioglycerol | 0.4 ml |
| Water to make | 1000 ml |
| pH | 6.20 |

The pH was adjusted with hydrochloric acid or sodium hydroxide.

| Bleaching Solution: | |
|---|---|
| Disodium ethylenediaminetetraacetate dihydrate | 2.0 g |
| Ammonium ethylenediaminetetraacetate iron (III) dihydrate | 120 g |
| Potassium bromide | 100 g |
| Ammonium nitrate | 10 g |
| Water to make | 1000 ml |
| pH | 5.70 |

The pH was adjusted with hydrochloric acid or sodium hydroxide.

| Fixing Solution: | |
|---|---|
| Ammonium thiosulfate | 80 g |
| Sodium sulfite | 5.0 g |
| Sodium bisulfite | 5.0 g |
| Water to make | 1000 ml |
| pH | 6.60 |

The pH was adjusted with hydrochloric acid or aqueous ammonia.

| Stabilizing Solution: | |
|---|---|
| Formalin (37%) | 5.0 ml |
| Polyoxyethylene-p-monononylphenyl ether (average degree of polymerization: 10) | 0.5 ml |
| Water to make | 1000 ml |
| pH | not adjusted |

Washing Water
City water

As a result of the evaluation of on color reproducibility of the color slides thus-obtained, it was found that the color slides obtained from Light-Sensitive Materials 501 to 508 of the present invention were excellent in color reproducibility of blue and green particularly in comparison with the color slide obtained from comparative Light-Sensitive Material 509.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least one silver halide red-sensitive emulsion layer containing at least one cyan coupler represented by formula (IV), (V), (VI), (VII), (VIII), (IX), (X), (XI), (XII), (XIII), (XIV), (XV), (XVI) or (XVII):

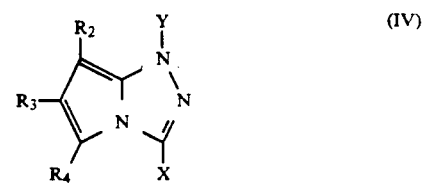

(IV)

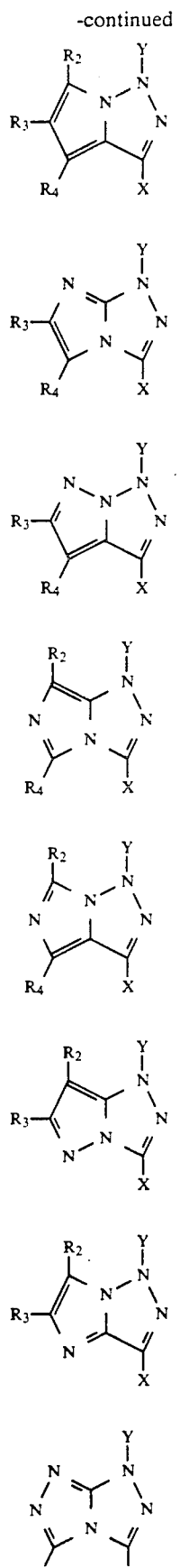

wherein in formula (IV) to (XVII), Y represents a hydrogen atom or a blocking group; X represents a hydrogen atom or a group which releases upon a reaction with an oxidation product of an aromatic primary amine color developing agent; $R_2$ and $R_4$ each represents a group which is substantially not released upon reaction with an oxidation product of an aromatic primary amine color developing agent; $R_3$ represents a hydrogen atom or a substituent; or $R_2$, $R_3$, $R_4$, or X may form a dimer, oligomer or polymer, provided that in formula (X), in a case where $R_2$ represents an alkoxycarbonyl group or an aryloxycarbonyl group, X does not represent an alkylthio group, a heterocyclic group, an acylamino group or an alkoxy group, and in a case where a dimer is formed by $R_2$, a bis type coupler is not formed by an alkylidene group.

2. A silver halide color photographic material as in claim 1, wherein $R_2$ and $R_4$ each represents a sulfamoyl group, a sulfonyl group, a sulfinyl group, or a carbon-containing group which is bonded at a carbon atom of the carbon-containing group and $R_3$ represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, an alkylthio group, an arylthio group, a heterocyclic thio group, an alkoxycarbonylamino group, a sulfonamido group, a carbamoyl group, an acyl group, a sulfamoyl group, a sulfonyl group, a sulfinyl group, an alkoxycarbonyl group or an aryloxycarbonyl group.

3. A silver halide color photographic material as in claim 1, wherein the releasable group is a halogen atom, an alkoxy group, an aryloxy group, an acyloxy group, a sulfonyloxy group, an amido group, an alkoxycarbonyloxy group, an aryloxycarbonyloxy group, an aliphatic, aromatic or heterocyclic thio group, an imido group, an N-heterocyclic group or an aromatic azo group.

4. A silver halide color photographic material as in claim 1, wherein Y represents a hydrogen atom, an acyl group having from 1 to 32 carbon atoms, an alkyl or aryl sulfonyl group having from 1 to 32 carbon atoms, an alkyl or aryl oxycarbonyl group having from 1 to 32 carbon atoms, an acyloxymethylene group having from 2 to 32 carbon atoms, a carbamoyl group having from 1 to 32 carbon atoms, or a group represented by formula (III)

wherein $Y_1$ and $Y_2$, which may be the same or different, each represents a nitro group, a cyano group, a carboxy group, an aryl group having from 6 to 32 carbon atoms, a heterocyclic group having from 1 to 32 carbon atoms, an acyl group having from 1 to 32 carbon atoms, an alkyl or aryl oxycarbonyl group having from 1 to 32 carbon atoms, an alkyl or aryl sulfonyl group having from 1 to 32 carbon atoms, a carbamoyl group having from 1 to 32 carbon atoms or a sulfamoyl group having from 0 to 32 carbon atoms.

5. A silver halide color photographic material as in claim 4, wherein Y represents a hydrogen atom, an acyl group or the group represented by the general formula (III).

6. A silver halide color photographic material as in claim 4, wherein Y is a hydrogen atom.

7. A silver halide color photographic material as in claim 1, wherein the total number of carbon atoms included in $R_2$, $R_3$, $R_4$, and X in each of formulae (IV) to (XVII) is at least 10.

8. A silver halide color photographic material as in claim 1, wherein the cyan coupler is present in an amount of from 0.001 mol to 1 mol per mol of light-sensitive silver halide present in the silver halide emulsion layer.

9. A silver halide color photographic material as in claim 1, wherein the silver halide color photographic material further comprises at least one blue-sensitive silver halide emulsion layer containing at least one yellow coupler and at least one green-sensitive silver halide emulsion layer containing at least one magenta coupler.

10. A silver halide color photographic material as in claim 1, wherein the silver halide emulsion layer containing the cyan coupler further contains a benzotriazole color fading preventing agent.

11. A silver halide color photographic material as in claim 9, wherein the blue-sensitive, green-sensitive and red-sensitive silver halide emulsion layers each comprises at least two layers having different photographic speeds.

12. A silver halide color photographic material as in claim 1, wherein the red-sensitive silver halide emulsion layer contains a silver chloride or silver chlorobromide emulsion.

13. A silver halide color photographic material as in claim 12, wherein the red-sensitive silver halide emulsion layer contains a silver chloride or silver chlorbromide emulsion having at least 90 mol % of the silver chloride content.

* * * * *